United States Patent
Chait et al.

(10) Patent No.: US 11,796,544 B1
(45) Date of Patent: Oct. 24, 2023

(54) PARTITIONING SYSTEMS AND METHODS FOR DETERMINING MULTIPLE TYPES OF CANCERS

(71) Applicant: Analiza, Inc., Bay Village, OH (US)

(72) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 0 days.

(21) Appl. No.: 18/030,849

(22) PCT Filed: Oct. 13, 2022

(86) PCT No.: PCT/US2022/046537
§ 371 (c)(1),
(2) Date: Apr. 7, 2023

(87) PCT Pub. No.: WO2023/076036
PCT Pub. Date: May 4, 2023

Related U.S. Application Data

(60) Provisional application No. 63/272,759, filed on Oct. 28, 2021.

(51) Int. Cl.
*G01N 33/574* (2006.01)
*G01N 33/50* (2006.01)

(52) U.S. Cl.
CPC ............ *G01N 33/57488* (2013.01); *G01N 33/5002* (2013.01)

(58) Field of Classification Search
CPC ......... G01N 33/57488; G01N 33/5002; G01N 33/48; G01N 33/68; G01N 33/6812; Y10T 436/145555; Y10T 436/17; Y10T 436/177692; Y10T 436/178459
USPC ................ 436/63, 86, 89, 96, 106, 116, 117
See application file for complete search history.

(56) References Cited

U.S. PATENT DOCUMENTS

| | | | |
|---|---|---|---|
| 5,008,204 A | 4/1991 | Stehling |
| 5,241,072 A | 8/1993 | Colon et al. |
| 5,340,474 A | 8/1994 | Kauvar |
| 5,734,024 A | 3/1998 | Zaslavsky |
| 5,769,074 A | 6/1998 | Barnhill et al. |
| 5,818,231 A | 10/1998 | Smith |
| 5,948,750 A | 9/1999 | Garsky et al. |
| 6,136,960 A | 10/2000 | Chait et al. |
| 6,642,009 B2 | 11/2003 | Hung |
| 7,011,955 B1 | 3/2006 | Stemmler et al. |
| 7,100,095 B2 | 8/2006 | Godse et al. |
| 7,247,498 B2 | 7/2007 | Godec et al. |
| 7,968,350 B2 | 6/2011 | Chait et al. |
| 8,099,242 B2 | 7/2012 | Chait et al. |
| 8,211,714 B2 | 7/2012 | Chait et al. |
| 9,354,229 B2 | 5/2016 | Chait et al. |
| 9,678,076 B2 | 6/2017 | Chait et al. |
| 2001/0016590 A1 | 8/2001 | Ahotupa et al. |
| 2001/0044431 A1 | 11/2001 | Gustavo |
| 2002/0045198 A1 | 4/2002 | Mikolajczyk |
| 2003/0162224 A1 | 8/2003 | Chait et al. |
| 2004/0229375 A1 | 11/2004 | Chait et al. |
| 2004/0236603 A1 | 11/2004 | Heller et al. |
| 2006/0240416 A1 | 10/2006 | Banerjee et al. |
| 2006/0255257 A1 | 11/2006 | Belgovskiy et al. |
| 2006/0269964 A1 | 11/2006 | Chait et al. |
| 2007/0128618 A1 | 6/2007 | Chait et al. |
| 2007/0198194 A1 | 8/2007 | Chait et al. |
| 2008/0050831 A1 | 2/2008 | Chait et al. |
| 2011/0166028 A1 | 7/2011 | Bergstrom et al. |

(Continued)

FOREIGN PATENT DOCUMENTS

| WO | WO 99/010522 A1 | 3/1999 |
|---|---|---|
| WO | WO 00/010674 A1 | 3/2000 |

(Continued)

OTHER PUBLICATIONS

Madeira et al. Journal of Chromatography A, vol. 1271, Nov. 19, 2012, pp. 10-16.*
Madeira et al. Journal of Physical Chemistry B, vol. 114, 2010, pp. 457-462.*
Madeira et al. Journal of Chromatography A, vol. 1229, Jan. 18, 2012, pp. 38-47.*
Da Silva et al. Journal of Chromatography A, vol. 1415, Aug. 28, 2015, pp. 1-10.*
Da Silva et al. Journal of Chromatography A, vol. 1425, Nov. 10, 2015, pp. 51-61.*
Ferreira et al. Journal of Chromatography A, vol. 1220, Dec. 8, 2011, pp. 14-20.*
Office Action from Canadian Application No. 2,466,663 dated May 6, 2010.
Office Action from Canadian Application No. 2,466,663 dated Oct. 17, 2011.

(Continued)

*Primary Examiner* — Maureen Wallenhorst
(74) *Attorney, Agent, or Firm* — Wolf, Greenfield & Sacks, P.C.

(57) ABSTRACT

The present disclosure generally relates to systems and methods for partitioning species. In some embodiments, such systems can be used for determining one or more types of cancer. For example, certain aspects are generally directed to aqueous multiphase partitioning systems that can be used, for example, for distinguishing between different types of cancers, diagnosing subjects with cancer, or the like. In some cases, such systems can be identified using solvent properties such as the solvent dipolarity/polarizability difference ($\Delta\pi^*$), the solvent hydrogen bond donor acidity difference ($\Delta\alpha$), the solvent hydrogen bond acceptor basicity difference ($\Delta\beta$), and the electrostatic property difference (c) between two phases of the partitioning system. These may be within certain ranges in accordance with various embodiments. Additionally, these ranges can be precisely tuned by controlling the compositions of the phases of the partitioning system to produce novel partitioning systems that are unexpectedly efficient at distinguishing between even relatively minor structural changes of proteins or other species, which accordingly can be used to distinguishing different types of cancers, or for other applications.

5 Claims, No Drawings

(56) References Cited

U.S. PATENT DOCUMENTS

| | | | |
|---|---|---|---|
| 2012/0088692 | A1 | 4/2012 | Chait et al. |
| 2012/0013727 | A1 | 6/2012 | Breniman et al. |
| 2012/0295300 | A1 | 11/2012 | Heng et al. |
| 2014/0065642 | A1 | 3/2014 | Chait et al. |
| 2015/0219655 | A1 | 8/2015 | Chait et al. |
| 2016/0238607 | A1 | 8/2016 | Chait et al. |
| 2019/0178891 | A1 | 6/2019 | Chait et al. |
| 2020/0209243 | A1 | 7/2020 | Chait et al. |
| 2022/0120664 | A1 | 4/2022 | Rognin et al. |

FOREIGN PATENT DOCUMENTS

| | | | |
|---|---|---|---|
| WO | WO 01/055698 | A1 | 8/2001 |
| WO | WO 03/016883 | A1 | 2/2003 |
| WO | WO 03/042694 | A2 | 5/2003 |
| WO | WO 2004/111655 | A1 | 12/2004 |
| WO | WO 2005/008247 | A2 | 1/2005 |
| WO | WO 2005/008247 | A3 | 1/2005 |
| WO | WO 2006/124100 | A2 | 11/2006 |
| WO | WO 2007/027561 | A2 | 3/2007 |
| WO | WO 2008/005043 | A2 | 1/2008 |
| WO | WO 2015/200302 | A2 | 12/2015 |

OTHER PUBLICATIONS

Office Action from European Application No. 02795636 dated Nov. 14, 2005.
Office Action from European Application No. 02795636 dated Feb. 8, 2007.
Office Action European Application No. 02795636 dated Oct. 27, 2008.
Written Opinion dated Apr. 30, 2003, for Application No. PCT/US2002/036519.
International Search Report dated Dec. 18, 2003, from International Application No. PCT/US2002/036519, filed Nov. 12, 2002.
Office Action from Canadian Application No. 2,528,535 dated May 5, 2009.
Office Action from Canadian Application No. 2,528,535 dated Mar. 15, 2010.
Office Action from Canadian Application No. 2,528,535 dated Nov. 23, 2011.
Office Action from Canadian Application No. 2,528,535 dated Jul. 23, 2012.
Office Action from European Application No. 04776693.6 dated Oct. 15, 2007.
Office Action from European Application No. 04776693.6 dated Oct. 10, 2008.
Office Action from European Application No. 04776693.6 dated Mar. 9, 2012.
International Search Report and Written Opinion, dated Nov. 23, 2004, for PCT/US2004/019343.
Office Action from European Application No. 02768567 dated Mar. 24, 2009.
International Search Report for PCT/US2002/026019 dated Oct. 3, 2002.
Written Opinion dated Apr. 30, 2003, from International Application No. PCT/US2002/026019.
International Preliminary Examination Report dated Oct. 15, 2003, from International Application No. PCT/US2002/026019.
Office Action from Australian Application No. 2006345702 dated Oct. 10, 2011.
Office Action from Australian Application No. 2006345702 dated Jan. 25, 2012.
Office Action from Chinese Application No. 200680052677.3 dated Oct. 27, 2011.
Office Action from Chinese Application No. 200680052677.3 dated Jul. 4, 2012.
Office Action European Application No. EP 06851492 dated Mar. 31, 2009.

International Search Report and Written Opinion for PCT/US2006/048344 dated Apr. 24, 2008.
International Preliminary Report on Patentability for PCT/US2006/048344 dated Jul. 3, 2008.
International Search Report and Written Opinion for Application No. PCT/US2013/054059 dated Dec. 10, 2013.
International Preliminary Report on Patentability for Application No. PCT/US2013/054059 dated Feb. 19, 2015.
International Search Report and Written Opinion dated Mar. 7, 2023, for Application No. PCT/US2022/046537.
[No Author Listed] Program listing of the Society of Biomolecular Screening 2002, Session 2A Technical Program for the $8^{th}$ Annual SBS Conference & Exhibition, Sep. 22-26, 2002, Netherlands Congress Centre, The Hague, The Netherlands.
[No Author Listed] Program listing of the Well-Characterized Biologics Conference 2002, California Separation Science Society, WCBP 2002, $6^{th}$ Symposium on the Interface of Regulatory and Analytical Sciences for Biotechnology Health Products, Jan. 27-30, 2002.
[No Author Listed] QSAR Introduction (web pages; last updated Jul. 2, 2007).
Albertsson et al., Separation processes in biotechnology. Aqueous two-phase separations. Bioprocess Technol. 1990;9:287-327.
Andrews et al., Affinity gel electrophoresis as a predicative technique in the fractionation of transgenic sheep milk proteins by affinity aqueous two-phase partitioning. Biotechnol Lett. 2000;22:1349-1353.
Arnoldi et al., Lipophilicity-Antifungal Activity Relationships for Some Isoflavonoid Phytoalexins. J Agric Food Chem. 1990; 38:834-838.
Atkinson et al., Trypsin and a-Chymotrypsin Partitioning in Polyethylene Glycol/Maltodextrin Aqueous-Two-Phase Systems. Food Bioprod. Proc. Jun. 1994;72:106-112.
Baker et al., In biomarkers we trust? Nat Biotechnol. Mar. 2005;23(3):297-304.
Bast et al., Translational crossroads for biomarkers. Clin Cancer Res. Sep. 1, 2005;11(17):6103-8.
Berggren et al., Substitutions of surface amino acid residues of cutinase probed by aqueous two-phase partitioning. BBA. 2000;1481:317-327.
Bevan et al., A High-Throughput Screening Method for the Determination of Aqueous Drug Solubility Using Laser Nephelometry in Microtiter Plates. Anal. Chem. 2000;72:1781-1787.
Bodnar et al. Exploiting the Complementary Nature of LC/MALDI/MS/MS and LC/ESI/MS/MS for Increased Proteome Coverage. American Society for Mass Spectrometry. 2003;14:971-979.
Chait, From Structure To Signature. $8^{th}$ Annual SBS Conference & Exhibition, Sep. 22-26, 2002, Netherlands Congress Centre, The Hague, The Netherlands.
Chait, HTS Technology for Analysis of Structural Signatures of Biomolecules: Methodology and Applications. California Separation Science Society, WCBP 2002, $6^{th}$ Symposium on the Interface of Regulatory and Analytical Sciences for Biotechnology Health Products, Jan. 27-30, 2002.
Durand et al., Protein Glycosylation and Diseases: Blood and Urinary Oligosaccharides as Markers for Diagnosis and Therapeutic Monitoring. Clinical Chemistry. 2000;46(6):795-805.
Everberg et al., Protein pre-fractionation in detergent-polymer aqueous two-phase systems for facilitated proteomic studies of membrane proteins. J Chromatogr A. 2004;1029:113-124.
Fedotoff et al., Influence of Serum Proteins on Conformation of Prostate-Specific Antigen. J. Biomol Struct. Dynamics. Apr. 1, 2012. 29(5): 1051-1064. DOI:10.1080/073911012010525030.
Guiliano, Aqueous Two-Phase Protein Partitioning Using Textile Dyes as Affinity Ligands. Anal. Biochem.1991;197:333-339.
Gulyaeva et al., Relative hydrophobicity of organic compounds measured by partitioning in aqueous two-phase systems. Journal of Chromatograph B.2000;743:187-194.
Guzzetta, Reverse Phase HPLC Basics for LC/MS. An IonSource Tutorial, published Jul. 22, 2001.
Harboe et al., Generation of Antibodies to the Signal Peptide of the MPT83 Lipoprotein of Mycobacterium tuberculosis. Scan. J. Immunol. 2002;55:82-87.

(56) References Cited

OTHER PUBLICATIONS

Hunger et al., The t(1;19)(q23;p13) results in consistent fusion of E2A and PBX1 coding sequences in acute lymphoblastic leukemias. Blood. 1991;77:687-693.
Kohwi et al., Amphipathic Lipid-Bound Protein Antigens in Mouse Bladder Carcinomas Detected by a Monoclonal Antibody. Biochemistry. 1984;23:5945-5950.
Kuboi, et al., Evaluation of Surface Hydrophobicities of Proteins Using Hydrophobic Interaction with Non-ionic Surfactants in Aqueous Two-Phase Partitioning Systems. Kagaku Kogaku Ronbunshu. 1993;19:446-453.
Labaer et al., So, you want to look for biomarkers (introduction to the special biomarkers issue). J Proteome Res. Jul.-Aug. 2005;4(4):1053-9.
Matsumura et al. A new concept for macromolecular therapeutics in cancer chemotherapy: mechanism of tumoritropic accumulation of proteins and the antitumor Smancs. Cancer Research. 1986;46:6387-92.
Müller et al., Real and Pseudo Oxygen Gradients in Ca-Alginate Beads Monitored During Polarographic $Po_2$-Measurements Using Pt-Needle Microelectrodes. Biotechnology and Bioengineering. 1994;44:617-625.
Peracaula et al., Altered glycosylation pattern allows the distinction between prostate-specific antigen (PSA) from normal and tumor origins. Glycobiology. Jun. 2003; 13(6):457-470.
Platt et al., QSAR in grossly underdetermined systems: Opportunities and issues. IBM Journal of Research and Development. 2001;45 (web page).
Richon, A et al., "An Introduction to QSAR Methodology," (web page; Oct. 1997) Accessed online at http://www.netsci.org/science/compchem/feature19.html.
Sakurai et al., Ligand- and Nuclear Factor-Dependent Change in Hydrophobicity of Thyroid Hormone $\beta_1$ Receptor. *Thyroid.* 1998;8(4):343-352.
Schena et al., Parallel human genome analysis: Microarray-based expression monitoring of 1000 genes. PNAS. Oct. 1996;93:10614-10619.
Singh et al., Gene expression correlates of clinical prostate cancer behavior. Cancer Cell, 2002;1:203-209.
Sniegoski, An Examination of the Concentration of Organic Components Water-Extracted From Petroleum Products. Water Research. 1975;9:421-423.
Stovsky et al., Prostate-specific Antigen/Solvent Interaction Analysis: A Preliminary Evaluation of a New Assay Concept for Detecting Prostate Cancer Using Urinary Samples. Urology. Sep. 2011. 78(3):601-605. Epub Jul. 23, 2011. doi: 10.1016/j.urology.2011.03.071.
Stovsky et al., PSA/SIA: A New Highly Sensitive and Specific Structure-Based Assay for Prostate Cancer (poster), AUA NC 82nd Annual Meeting, Chicago, IL, Sep. 24-27, 2008.
Takano et al. Measuring the Solubility of Liquid Organic Compounds in Water. Journal of the Chemical Society of Japan. 1985, (11):2116-2119.
Takano et al., Solubility Measurement of Liquid Organic Compounds in Water. CAS Online. 1985. 105:60254.
Yan, Detection by ozone-induced chemiluminescence in chromatography. Journal of Chromatography. 1999;842:267-308.
Zaslavsky et al., A New Method for Analysis of Components in a Mixture without Preseparation: Evaluation of the Concentration Ratio and Protein-Protein Interaction. Analytical Biochemistry. 2001;296:262-269.
Zaslavsky, Aqueous Two-Phase Partitioning (Book) Marcel Dekker, New York, Ch. 1-10 (1995).
Zaslavsky, Characteristics of Protein-Aqueous Medium Interactions Measured by Partition in Aqueous Ficoll-Dextran Biphasic System. J. Chromatogr. 1983;260:329-336.
Zaslavsky et al., Analytical applications of partitioning in aqueous two-phase systems: Exploring protein structural changes and protein-partner interactions in vitro and in vivo by solvent interaction analysis method. Biochim Biophys Acta. May 2016;1864(5):622-44. doi: 10.1016/j.bbapap.2016.02.017. Epub Feb. 23, 2016.
Zhong et al., Identification of prohibitin 1 as a potential prognostic biomarker in human pancreatic carcinoma using modified aqueous two-phase partition system combined with 2D-MALDI-TOF-TOF-MS/MS. Tumour Biol. Feb. 2015;36(2):1221-31. doi: 10.1007/s13277-014-2742-y. Epub Oct. 25, 2014.
U.S. Appl. No. 16/273,253, filed Feb. 12, 2019, Chait et al.
CA 2466663, May 6, 2010, Canadian Office Action.
CA 2466663, Oct. 17, 2011, Canadian Office Action.
EP 02795636, Nov. 14, 2005, European Office Action.
EP 02795636, Feb. 8, 2007, European Office Action.
EP 02795636, Oct. 27, 2008, European Office Action.
PCT/US2002/036519, Apr. 30, 2003, Witten Opinion.
PCT/US2002/036519, Dec. 18, 2003, International Search Report.
CA 2528535, May 5, 2009, Canadian Office Action.
CA 2528535, Mar. 15, 2010, Canadian Office Action.
CA 2528535, Nov. 23, 2011, Canadian Office Action.
CA 2528535, Jul. 23, 2012, Canadian Office Action.
EP 04776693.6, Oct. 15, 2007, European Office Action.
EP 04776693.6, Oct. 10, 2008, European Office Action.
EP 04776693.6, Mar. 9, 2012, European Office Action.
PCT/US2004/019343, Nov. 23, 2004, International Search Report and Written Opinion.
EP 02768567, Mar. 24, 2009, European Office Action.
PCT/US2002/026019, Oct. 3, 2002, International Search Report.
PCT/US2002/026019, Apr. 30, 2003, Written Opinion.
PCT/US2002/026019, Oct. 15, 2003, International Preliminary Report on Patentability.
AU2006342702, Oct. 10, 2011, Australian Office Action.
AU2006342702, Jan. 25, 2012, Australian Office Action.
CN200680052677.3, Oct. 27, 2011, Chinese Office Action.
CN200680052677.3, Jul. 4, 2012, Chinese Office Action.
EP06851492, Mar. 31, 2009, European Office Action.
PCT/US2006/048344, Apr. 24, 2008, International Search Report and Written Opinion.
PCT/US2006/048344, Jul. 3, 2008, International Preliminary Report on Patentability.
PCT/US2013/054059, Dec. 10, 2013, International Search Report and Written Opinion.
PCT/US2013/054059, Feb. 19, 2015, International Preliminary Report on Patentability.
PCT/US2022/046537, Mar. 7, 2023, Internarional Search Report and Written Opinion.

\* cited by examiner

US 11,796,544 B1

PARTITIONING SYSTEMS AND METHODS FOR DETERMINING MULTIPLE TYPES OF CANCERS

RELATED APPLICATIONS

This application is a national stage filing under 35 U.S.C. § 371 of International Patent Application Serial No. PCT/US2022/046537, filed Oct. 13, 2022, entitled "Partitioning Systems and Methods for Determining Multiple Types of Cancers," which claims the benefit of U.S. Provisional Patent Application Ser. No. 63/272,759, filed Oct. 28, 2021, entitled "Partitioning Systems and Methods for Determining Multiple Types of Cancers," each of which is incorporated herein by reference in its entirety.

FIELD

The present disclosure generally relates to systems and methods for partitioning species. In some embodiments, such systems can be used for determining one or more types of cancer.

BACKGROUND

Aqueous partitioning systems are generally known to be sensitive for structural changes in small molecules, proteins, viruses, etc. See, for example, U.S. Pat. Nos. 7,968,350; 8,099,242; 8,211,714; or 9,354,229, each incorporated herein by reference in its entirety. These partitioning systems can be used, for example, to detect structural modifications with proteins, e.g., that are produced by cancer cells. For instance, cancers may alter such proteins by alternative splicing, conformational changes, posttranslational modifications (especially certain glycosylation), protein-protein interactions, or the like. Accordingly, such aqueous partitioning systems have previously been used to distinguish between cancer and non-cancer conditions. However, partitioning systems for distinguishing between different types of cancers have not previously been described.

SUMMARY

The present disclosure generally relates to systems and methods for partitioning species. In some embodiments, such systems can be used for determining one or more types of cancer. The subject matter of the present disclosure involves, in some cases, interrelated products, alternative solutions to a particular problem, and/or a plurality of different uses of one or more systems and/or articles.

One aspect is generally directed to a composition comprising an aqueous two-phase partitioning system having a first phase and a second phase, wherein the aqueous two-phase partitioning system has (i) a solvent dipolarity/polarizability difference between the first phase and the second phase ($\Delta\pi^*$) of $-0.175+/-0.007$, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$; (ii) a solvent hydrogen bond donor acidity difference between the first phase and the second phase ($\Delta\alpha$) of $0.001+/-0.035$, wherein $\Delta\alpha$ is determined as a difference between hydrogen bond donor acidity (a) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932)[(28591/\lambda)-3.335]$, and calculating $\alpha$ in each phase as $0.0649\ E_T(30)-2.03-0.72\pi^*$; (iii) a solvent hydrogen bond acceptor basicity difference between the first phase and the second phase ($\Delta\beta$) of $-0.050+/-0.021$, wherein $\Delta\beta$ is determined as a difference between hydrogen bond acceptor basicity ($\beta$) of the first phase and the second phase, and $\beta$ is determined separately in each phase by measuring a wavenumber ($v_2$) in cm$^{-1}$ of a longest wavelength absorption band of 4-nitrophenol in each phase, and calculating $\beta$ in each phase as $0.346(35.045-v_2)-0.57\pi^*$; and (iv) an electrostatic property difference between the first phase and the second phase (c) of $0.020+/-0.135$, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E\ N_c$ to determine c and E, wherein Table I is:

TABLE I

| Salt | $N_c$ |
| --- | --- |
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. |

Another aspect is generally directed to a composition, comprising an aqueous two-phase partitioning system having a first phase and a second phase, wherein the aqueous two-phase partitioning system has (i) a solvent dipolarity/polarizability difference between the first phase and the second phase ($\Delta\pi^*$) selected from a row within Table II, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$; (ii) a solvent hydrogen bond donor acidity difference between the first phase and the second phase ($\Delta\alpha$) selected from the row within Table II, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932)[(28591/\lambda)-3.335]$, and calculating $\alpha$ in each phase as $0.0649\ E_T(30)-2.03-0.72\pi^*$; (iii) a solvent hydrogen bond acceptor basicity difference between the first phase and the second phase ($\Delta\beta$) selected from the row within Table II, wherein $\Delta\beta$ is determined as a difference between hydrogen bond acceptor basicity ($\beta$) of the first phase and the second phase, and $\beta$ is determined separately in each phase by measuring a wavenumber ($v_2$) in cm$^{-1}$ of a longest wavelength absorption band of 4-nitrophenol in each phase, and calculating $\beta$ in each phase as $0.346(35.045-v_2)-0.57\pi^*$; and (iv) an electrostatic property difference between the first phase and the second phase (c) selected from the row within Table II, wherein c is determined by separately partitioning each dinitrophenylated amino acid sodium salt in Table I in the aqueous two-phase partitioning system, measuring the partitioning coefficient (K) of each, and regressing K and methylene group equivalents ($N_c$) of each dinitrophenylated amino acid sodium salt in Table I to $\log_{10} K = c + E\ N_c$ to determine c and E, wherein Table I is:

TABLE I

| Salt | $N_c$ |
| --- | --- |
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. | and wherein Table II is:

TABLE II

| Δπ* | Δα | Δβ | c |
| --- | --- | --- | --- |
| −0.175 +/− 0.007 | 0.001 +/− 0.035 | −0.050 +/− 0.021 | 0.020 +/− 0.135 |
| 0.005 +/− 0.008 | −0.380 +/− 0.095 | −0.020 +/− 0.019 | 0.295 +/− 0.184 |
| −0.105 +/− 0.040 | −0.183 +/− 0.048 | 0.060 +/− 0.020 | 0.575 +/− 0.125 |
| −0.040 +/− 0.040 | −0.270 +/− 0.052 | 0.021 +/− 0.022 | 0.050 +/− 0.060 |
| 0.035 +/− 0.040 | −0.088 +/− 0.050 | 0.102 +/− 0.023 | 0.775 +/− 0.125. |

Yet another aspect is generally directed to a composition, comprising an aqueous two-phase partitioning system having a first phase and a second phase, wherein the aqueous two-phase partitioning system has: (i) a solvent dipolarity/polarizability difference between the first phase and the second phase (Δπ*) selected from a row within Table II; (ii) a solvent hydrogen bond donor acidity difference between the first phase and the second phase (Δα) selected from the row within Table II; (iii) a solvent hydrogen bond acceptor basicity difference between the first phase and the second phase (Δβ) selected from the row within Table II; and (iv) an electrostatic property difference between the first phase and the second phase (c) of selected from the row within Table II, wherein Table II is:

TABLE II

| Δπ* | Δα | Δβ | c |
| --- | --- | --- | --- |
| −0.175 +/− 0.007 | 0.001 +/− 0.035 | −0.050 +/− 0.021 | 0.020 +/− 0.135 |
| 0.005 +/− 0.008 | −0.380 +/− 0.095 | −0.020 +/− 0.019 | 0.295 +/− 0.184 |
| −0.105 +/− 0.040 | −0.183 +/− 0.048 | 0.060 +/− 0.020 | 0.575 +/− 0.125 |
| −0.040 +/− 0.040 | −0.270 +/− 0.052 | 0.021 +/− 0.022 | 0.050 +/− 0.060 |
| 0.035 +/− 0.040 | −0.088 +/− 0.050 | 0.102 +/− 0.023 | 0.775 +/− 0.125. |

Still another aspect is generally drawn to a composition, comprising an aqueous multi-phase partitioning system that exhibits a first partition coefficient for a solute arising from a subject with a first cancer type, a second partition coefficient for the solute arising from a subject with a second cancer type, and a third partition coefficient for the solute arising from a subject not having either the first or second cancer types.

Yet another aspect is generally drawn to a composition, comprising an aqueous two-phase partitioning system having a first phase and a second phase, wherein the aqueous two-phase partitioning system has (i) a solvent dipolarity/polarizability difference between the first phase and the second phase (Δπ*) of 0.005+/−0.008, wherein Δπ* is determined as a difference between dipolarity/polarizability (π*) of the first phase and the second phase, and π* is determined separately in each phase by measuring a wavenumber ($v_1$) in cm$^{-1}$ of a longest wavelength absorption band of 4-nitroanisole in each phase, and calculating π* in each phase as 0.427(34.12−$v_1$); (ii) a solvent hydrogen bond donor acidity difference between the first phase and the second phase (Δα) of −0.380+/−0.095, wherein Δα is determined as a difference between hydrogen bond donor acidity (α) of the first phase and the second phase, and α is determined separately in each phase by measuring a maximum wavelength (λ) in nm of an absorption band of carboxylated pyridinium N-phenolate betaine in each phase, calculating a solvent polarity ($E_T(30)$) in each phase as (1/0.932) [(28591/λ)−3.335], and calculating α in each phase as 0.0649 $E_T(30)$−2.03−0.72π*; (iii) a solvent hydrogen bond acceptor basicity difference between the first phase and the second phase (Δβ) of −0.020+/−0.019, wherein Δβ is determined as a difference between hydrogen bond acceptor basicity (β) of the first phase and the second phase, and β is determined separately in each phase by measuring a wavenumber ($v_2$) in cm$^{-1}$ of a longest wavelength absorption band of 4-nitrophenol in each phase, and calculating β in each phase as 0.346(35.045−$v_2$)−0.57π*; and (iv) an electrostatic property difference between the first phase and the second phase (c) of 0.295+/−0.184, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E\ N_c$ to determine c and E, wherein Table I is:

TABLE I

| Salt | $N_c$ |
| --- | --- |
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. |

Another aspect is generally drawn to a composition, comprising an aqueous two-phase partitioning system having a first phase and a second phase, wherein the aqueous two-phase partitioning system has (i) a solvent dipolarity/polarizability difference between the first phase and the second phase (Δπ*) of −0.105+/−0.040, wherein Δπ* is determined as a difference between dipolarity/polarizability (π*) of the first phase and the second phase, and π* is determined separately in each phase by measuring a wavenumber ($v_1$) in cm$^{-1}$ of a longest wavelength absorption band of 4-nitroanisole in each phase, and calculating π* in each phase as 0.427(34.12−$v_1$); (ii) a solvent hydrogen bond donor acidity difference between the first phase and the second phase (Δα) of −0.183+/−0.048, wherein Δα is determined as a difference between hydrogen bond donor acidity (α) of the first phase and the second phase, and α is determined separately in each phase by measuring a maximum wavelength (λ) in nm of an absorption band of carboxylated pyridinium N-phenolate betaine in each phase, calculating a solvent polarity ($E_T(30)$) in each phase as (1/0.932) [(28591/λ)−3.335], and calculating α in each phase as 0.0649 $E_T(30)$−2.03−0.72π*; (iii) a solvent hydrogen bond acceptor basicity difference between the first phase and the second phase (Δβ) of 0.060+/−0.020, wherein Δβ is determined as a difference between hydrogen bond acceptor basicity (β) of the first phase and the second phase, and β is determined separately in each phase by measuring a wavenumber ($v_2$) in cm$^{-1}$ of a longest wavelength absorption band of 4-nitrophenol in each phase, and calculating β in each phase as 0.346(35.045−$v_2$)−0.57π*; and (iv) an electrostatic property difference between the first phase and the second phase (c) of 0.575+/−0.125, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. |

Still another aspect is generally drawn to a composition, comprising an aqueous two-phase partitioning system having a first phase and a second phase, wherein the aqueous two-phase partitioning system has (i) a solvent dipolarity/polarizability difference between the first phase and the second phase ($\Delta\pi^*$) of $-0.040+/-0.040$, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in $cm^{-1}$ of a longest wavelength absorption band of 4-nitroanisole in each phase, and calculating $\pi^*$ in each phase as $0.427(34.12-v_1)$; (ii) a solvent hydrogen bond donor acidity difference between the first phase and the second phase ($\Delta\alpha$) of $-0.270+/-0.052$, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932) [(28591/\lambda)-3.335]$, and calculating $\alpha$ in each phase as $0.0649 E_T(30)-2.03-0.72\pi^*$; (iii) a solvent hydrogen bond acceptor basicity difference between the first phase and the second phase (A) of $0.021+/-0.022$, wherein $\Delta\beta$ is determined as a difference between hydrogen bond acceptor basicity ($\beta$) of the first phase and the second phase, and $\beta$ is determined separately in each phase by measuring a wavenumber ($v_2$) in $cm^{-1}$ of a longest wavelength absorption band of 4-nitrophenol in each phase, and calculating $\beta$ in each phase as $0.346(35.045-v_2)-0.57\pi^*$; and (iv) an electrostatic property difference between the first phase and the second phase (c) of $0.050+/-0.060$, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. |

Yet another aspect is generally drawn to a composition, comprising an aqueous two-phase partitioning system having a first phase and a second phase, wherein the aqueous two-phase partitioning system has (i) a solvent dipolarity/polarizability difference between the first phase and the second phase ($\Delta\pi^*$) of $0.035+/-0.040$, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in $cm^{-1}$ of a longest wavelength absorption band of 4-nitroanisole in each phase, and calculating $\pi^*$ in each phase as $0.427(34.12-v_1)$; (ii) a solvent hydrogen bond donor acidity difference between the first phase and the second phase ($\Delta\alpha$) of $-0.088+/-0.050$, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932) [(28591/\lambda)-3.335]$, and calculating $\alpha$ in each phase as $0.0649 E_T(30)-2.03-0.72\pi^*$; (iii) a solvent hydrogen bond acceptor basicity difference between the first phase and the second phase (A) of $0.102+/-0.023$, wherein $\Delta\beta$ is determined as a difference between hydrogen bond acceptor basicity ($\beta$) of the first phase and the second phase, and $\beta$ is determined separately in each phase by measuring a wavenumber ($v_2$) in $cm^{-1}$ of a longest wavelength absorption band of 4-nitrophenol in each phase, and calculating $\beta$ in each phase as $0.346(35.045-v_2)-0.57\pi^*$; and (iv) an electrostatic property difference between the first phase and the second phase (c) of $0.775+/-0.125$, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-n-octanoic acid, Na salt | 6.30. |

Another aspect is generally drawn to a method, comprising providing at least a first aqueous multi-phase partitioning system and a second aqueous multi-phase partitioning system substantially compositionally identical to the first partitioning system; determining a first cancer in a first subject by adding a first sample from the first cancer subject to the first partitioning system and determining partitioning of a solute in the first sample within the first partitioning system; and determining a second cancer in a second subject by adding a second sample from the second cancer subject to the second partitioning system and determining partitioning of the solute in the second sample within the second partitioning system.

In another aspect, the present disclosure encompasses methods of making one or more of the embodiments described herein, for example, an aqueous partitioning system. In still another aspect, the present disclosure encompasses methods of using one or more of the embodiments described herein, for example, an aqueous partitioning system.

Other advantages and novel features of the present disclosure will become apparent from the following detailed description of various non-limiting embodiments of the disclosure.

DETAILED DESCRIPTION

The present disclosure generally relates to systems and methods for partitioning species. In some embodiments, such systems can be used for determining one or more types of cancer. For example, certain aspects are generally directed to aqueous multi-phase partitioning systems that can be used, for example, for distinguishing between different types of cancers, diagnosing subjects with cancer, or the like. In some cases, such systems can be identified using solvent properties such as the solvent dipolarity/polarizability difference ($\Delta\pi^*$), the solvent hydrogen bond donor acidity difference ($\Delta\alpha$), the solvent hydrogen bond acceptor basicity difference ($\Delta\beta$), and the electrostatic property difference (c) between two phases of the partitioning system. These may be within certain ranges in accordance with various embodiments. Additionally, these ranges can be precisely tuned by controlling the compositions of the phases of the partitioning system to produce novel partitioning systems that are unexpectedly efficient at distinguishing between even relatively minor structural changes of proteins or other species, which accordingly can be used to distinguishing different types of cancers, or for other applications.

One aspect is generally directed to a single partitioning system that can be used for determining different partition coefficients (K) of same proteins for samples corresponding for different cancers, or other conditions. This is surprising in view of previous studies that have shown that the same protein, partitioned for all cancer samples, would have behaved the same, i.e., with similar K values for all cancers, indicating that the same protein would partition in the same way, even though arising from different cancers.

In general, changes to the structure of the protein due to cancer (or other conditions) that are uncovered using partitioning systems such as those described herein would have been expected to be similar across different cancer, given that cancer biology leading to such changes is similar, e.g., posttranslational modifications, metabolic changes, etc. However, surprisingly, some types of partitioning systems, including those described herein, may produce different partitioning behaviors for the same protein arising from different types of cancers. Partitioning systems exhibiting such unusual behaviors are difficult to identify, and cannot be identified merely by inspecting the components forming the partitioning system, given the vast extent of the chemical space forming such systems. Instead, such partitioning behavior depends on certain solvent properties such as the solvent dipolarity/polarizability difference ($\Delta\pi^*$), the solvent hydrogen bond donor acidity difference ($\Delta\alpha$), the solvent hydrogen bond acceptor basicity difference ($\Delta\beta$), and the electrostatic property difference (c). These may be controlled not only by the components forming the partitioning system, but also by the concentrations of those components. It is believed that compositions exhibiting solvent properties such as those described herein are important for identifying partitioning systems that exhibit the right properties to allow proteins arising from different cancers to partition differently, for example, in such a way that allows the cancer that the protein arises from to be determined. Accordingly, various embodiments such as those described herein are generally directed to partitioning systems exhibiting certain combinations of solvent properties. These can be described, measured, and determined as discussed herein.

Note that different partitioning systems with different chemical components or ingredients may still exhibit the same solvent properties. Without wishing to be bound by any theory, it is believed that the interactions of a protein (or other species) with two or more solvents with different intermolecular properties are governed by certain solvent properties such as those described herein. Accordingly, as discussed herein, certain types of partitioning systems are described by their solvent properties. While the solvent properties described and utilized in certain embodiments may be convenient to use and/or experimentally accessible, other properties could also be used to describe solvent structures of interest and/or to analyze solvent:solute molecular interactions, including those leading to observed differential partitioning in aqueous two-phase partitioning systems. In addition, the partitioning system may comprise two phases, or more than two phases in some cases. Additionally, in some embodiments, some or all of the phases within the partitioning system may be aqueous.

Cancer is generally caused by mutations, which can result in changes to coding, translation, and/or post-translational events during protein synthesis, including some well-known global intercellular environmental modifications due to metabolic changes, etc. All of these can combine to result in a variety of structural alterations to proteins or other species, which can be correlated with cancer in proteins and their interactions. This property can be used for diagnostics or treatment purposes, e.g., as discussed herein.

It is important to note that certain modifications to the structure are found consistently amongst proteins produced in the altered metabolic environment of cancer cells, e.g., certain posttranslational modification such as glycosylation. Such structural changes can affect the entire repertoire of protein biomarkers of interest, such as glycoproteins, or other biomarkers such as those described herein. Therefore, although each protein may have different primary, secondary, and tertiary structure, certain alterations to the higher order structure in the presence of cancer metabolism are specific, and can be determined using generalized tools such as those described herein, which may be able to resolve such differences.

In certain aspects, when describing the specific composition of a partitioning system, its starting chemical composition or components, e.g., amount and type of polymers, salts, etc., could be used. This description, however, does not adequately describe the molecular properties of the solvent phases that give rise to the observed partitioning behavior of a solute (e.g., a protein) via its differential interaction with such phases. To the contrary, these solvent-solute molecular interactions are exceedingly complex. A thermodynamic phase diagram can be experimentally constructed from the initial starting chemical components of the phases of the partitioning system, but such a phase diagram will often be inadequate to accurately describe the observed partitioning behavior of a solute within the partitioning system. Thus, detailing the initial chemical components of the partitioning system via its starting chemical ingredients does not adequately predict specific relationships between the partitioning system and the partitioning behavior of the solute. Indeed, different partitioning systems with similar chemical compositions may exhibit substantially different partitioning behaviors for a solute, while conversely, substantially different starting chemical compositions may result in partitioning systems exhibiting the same partitioning behavior for the same solute.

As discussed herein, an improved methodology of predicting the observed partitioning behavior of a solute in a partitioning system uses certain solvent properties such as the solvent dipolarity/polarizability difference ($\Delta\pi^*$), the solvent hydrogen bond donor acidity difference ($\Delta\alpha$), the solvent hydrogen bond acceptor basicity difference ($\Delta\beta$), and the electrostatic property difference (c). These are discussed in more detail herein. A variety of specific combinations of these solvent properties gives rise to novel formulations that are surprisingly effective at partitioning certain types of solutes (e.g., proteins). For example, certain partitioning systems described herein can be used to distinguish between different types of cancers. For example, the same protein, arising from different subjects (e.g., different people with different cancers) may partition different, e.g., depending on the type of cancer. As mentioned, this is surprising since previous studies have shown, as expected, that the same protein, partitioned for all cancer samples, would have behaved the same, even if arising from different types of cancers.

In some embodiments, the partitioning systems may in general be relatively sensitive to differences in the structure of certain solutes (e.g., proteins or protein biomarkers) corresponding to different cancers that are described in terms of specific solvent properties. In one embodiment, four solvent properties are used to define the solute-solvent interactions between the various phases that form the basis of the novel partitioning systems described herein. Such solvent properties may be achieved, in certain embodiments, by certain combinations of solvents, polymers, salts, etc., which can be determined as described herein.

Thus, in some aspects, the same protein (or other solute), made in different cancers, can be determined using the same partitioning system. The variability of partitioning behavior of the protein may be consistent on the average for each cancer, but different between cancers. Thus, a sample (for example a blood or other sample obtained clinically) may be introduced into a single partitioning system, and then following partitioning, the protein could be determined by measuring its concentration in the phases of the partitioning system, e.g., with a suitable immunoassay (for example, ELISA). The same could be repeated in some cases for additional proteins (or other solutes) in the same sample being partitioned using their corresponding immunoassays. Such partitioning behaviors (e.g., as a single protein or a signature comprised of multiple proteins, etc.) may then be determined, for example, as a partition coefficient (K), or other suitable metric. In some embodiments, comparing partition coefficients (or other metrics) to previously known values, e.g., corresponding to partition coefficients obtained for different cancers may then be used to determine the type of cancer, or otherwise determine the clinical phenotype of the sample. Non-limiting examples of cancers include throat cancer, stomach cancer, pancreatic cancer, brain cancer, lung cancer, cervical cancer, prostate cancer, breast cancer, testicular cancer, ovarian cancer, oral cancer, throat cancer, esophagus cancer, and intestinal cancer and intestinal cancer. Other examples of cancer are discussed in more detail below.

In some cases, more than one solute or species (e.g., more than one protein) may be determined, e.g., in the same or different partitioning systems, e.g., using their corresponding immunoassays or other determination methods. In some cases, e.g., as discussed herein, the same partitioning system may exhibit different types of partitioning behaviors for different cancer types for two or more of the solutes. Thus, by determining multiple solvents, the clinical diagnostics or performance, e.g., in terms of sensitivity and/or specificity, may be improved in some embodiments.

Without wishing to be bound by any theory, partitioning behavior of a solute (e.g., a protein) in a partitioning system formed by two nonionic polymers or by a single polymer and salt is believed to be governed by different types of interactions between the solute and aqueous media in the two phases. These include: (1) dipole-dipole and dipole-induced dipole interactions (quantifiable as $\pi^*$, as discussed herein); (2) hydrogen bond interactions with water serving as a donor of hydrogen bonds (quantifiable as a, as discussed herein); (3) hydrogen bond interactions with water serving as an acceptor of hydrogen bonds (quantifiable as $\beta$, as discussed herein); (4) electrostatic ion-dipole and ion-ion interactions (quantifiable as c, as discussed herein). These solvent properties, once quantified, may describe solute partition behavior with a relatively high degree of accuracy. In one set of embodiments, these may be used to predict the solute partition coefficient in a partitioning system, such as an aqueous two-phase system, using:

$$\log K_s = S_s \Delta \pi^* + B_s \Delta \alpha + A_s \Delta \beta + C_s c,$$

where $K_s$ is the solute partition coefficient; $\Delta \pi^*$, $\Delta \alpha$, $\Delta \beta$, and c are the differences between the solvent properties of the top and bottom phases (solvent dipolarity/polarizability, hydrogen-bond donor acidity, hydrogen-bond acceptor basicity, and electrostatic properties, respectively); $S_s$, $B_s$, $A_s$, and $C_s$ are constants (solute-specific coefficients) that describe the complementary interactions of the solute with the solvent media in the coexisting phases; and the subscript 's' designates the solute.

The solvent dipolarity/polarizability, solvent hydrogen-bond donor acidity, and solvent hydrogen-bond acceptor basicity of each phase of a partitioning system may be quantified, in some embodiments, using solvatochromic dyes, such as 4-nitroanizole (for estimating solvent dipolarity/polarizability, $\pi^*$), 4-nitrophenol (for estimating solvent hydrogen bond acceptor ability, $\beta$), and the water soluble solvatochromic Reichardt's carboxylated betaine dye, sodium {2,6-diphenyl-4-[4-(4-carboxylato-phenyl)-2,6-diphenylpyridinium-1-yl])phenolate} (for estimating solvent hydrogen bond donor ability, a). Example protocols for measuring such solvent properties are described in Madeira, et al., "Solvent Properties Governing Solute Partitioning in Polymer/Polymer Aqueous Two-Phase Systems: Nonionic Compounds," *J. Phys. Chem. B.*, 114(1):457-462, 2010; and Madeira, et al., "Solvent Properties Governing Protein Partitioning in Polymer/Polymer Aqueous Two-Phase Systems," *J. Chromatogr. A*, 1218(10):1379-1384, 2011, each incorporated herein by reference in its entirety. The differences between the solvent properties of the phases of a partitioning system (i.e., $\Delta$) are calculated as those between the phases of the partitioning system.

The solvent dipolarity/polarizability difference ($\Delta \pi^*$) can be determined as a difference between dipolarity/polarizability ($\pi^*$) of the phases of the partitioning system. $\pi^*$ is generally a measure of the stabilizing extent of a solvent for a charge or a dipole, and can be altered in a partitioning system by using charged nucleic acids such as arginine, lysine, etc. $\pi^*$ can be determined separately in each phase by measuring a wavenumber ($v_1$) in $cm^{-1}$ of a longest wavelength absorption band of 4-nitroanisole in each phase, and calculating $\pi^*$ in each phase as $0.427(34.12-v_1)$.

The solvent hydrogen bond donor acidity difference ($\Delta \alpha$) can be determined as a difference between hydrogen bond donor acidity ($\alpha$) of the phases of the partitioning system. $\alpha$ is generally a measure of the tendency of solvent molecules to donate a proton in a hydrogen bond with the solute molecules, and can be altered in a partitioning system by using osmolytes such as trimethylamine N-oxide (TMAO), dimethylsulfoniopropionate, sarcosine, betaine, glycerophosphorylcholine, myo-inositol, taurine, glycine, or the like. α can be determined separately in each phase by measuring a maximum wavelength (λ) in nm of an absorption band of carboxylated pyridinium N-phenolate betaine in each phase, calculating a solvent polarity ($E_T(30)$) in each phase as $(1/0.932) [(28591/\lambda)-3.335]$, and calculating α in each phase as $0.0649 \, E_T(30)-2.03-0.727*$.

The solvent hydrogen bond acceptor basicity difference (Δβ) can be determined as a difference between hydrogen bond acceptor basicity (β) of the phases of the partitioning system. β is generally a measure of the ability of a solvent to accept a hydrogen bond in solute-solvent hydrogen-bond interaction, or to donate an electron pair in a solute-solvent coordinate bond. It can be altered in a partitioning system by adding sugars such as glucose, trehalose, sucrose, galactose, fructose, etc. R can be determined separately in each phase by measuring a wavenumber ($v_2$) in $cm^{-1}$ of a longest wavelength absorption band of 4-nitrophenol in each phase, and calculating β in each phase as $0.346(35.045-v_2)-0.577*$.

The difference between the electrostatic properties of the phases (c) may be determined by analysis of partition coefficients of a homologous series of sodium salts of dinitrophenylated (DNP-) amino acids with aliphatic alkyl side chains (DNP-glycine, DNP-alanine, DNP-norvaline, DNP-norleucine, and DNP-β-amino-n-octanoic acid). These compounds are water soluble and colored, which makes it convenient to assay their concentrations in the phases using direct absorption measurements with UV-VIS spectrophotometer at 360 nm. When the logarithms of partition coefficients of the DNP-amino acid Na salts are plotted against the length of the side chain expressed in an equivalent number of methylene groups (Ne), a linear curve is observed. This curve may be described as:

$$\log K^i_{DNP-AA} = c^i + E^i N_c,$$

where $K_{DNP-AA}$ is the partition coefficient of of the DNP-amino acid Na salts; $N_c$ is the equivalent number of $CH_2$ groups in the side chain, E and c are constants for a given $i^{th}$ ATPS characterizing the difference between the relative hydrophobicity and electrostatic properties of the phases.

Accordingly, in some embodiments, c may be determined by separately partitioning various dinitrophenylated amino acid sodium salts in a partitioning system, measuring the partitioning coefficient (K) of each sodium salt, and regressing K and methylene group equivalents ($N_c$) of each sodium salt to $\log_{10} K = c + E \, N_c$ to determine c and E. For example, the dinitrophenylated amino acid sodium salts may be dinitrophenylated alanine sodium salt (with an $N_c$ of 1.31), dinitrophenylated norvaline sodium salt (with an $N_c$ of 2.65), dinitrophenylated norleucine sodium salt (with an $N_c$ of 3.75), and dinitrophenylated β-amino-n-octanoic acid, sodium salt (with an $N_c$ of 6.30).

In general, c is generally a measure of electrostatic effects that arise due to the interaction of solute charges among themselves and with solvent and ion charges, and can be altered in a partitioning system by adding salt such as NaCl, KCl, $Cs_2SO_4$, or other salts, including any of those described herein.

Non-limiting examples of partitioning systems with specific values for the above solvent properties which have not previously been described are as follows:

| Δπ* | Δα | Δβ | c |
|---|---|---|---|
| −0.175 +/− 0.007 | 0.001 +/− 0.035 | −0.050 +/− 0.021 | 0.020 +/− 0.135 |
| 0.005 +/− 0.008 | −0.380 +/− 0.095 | −0.020 +/− 0.019 | 0.295 +/− 0.184 |
| −0.105 +/− 0.040 | −0.183 +/− 0.048 | 0.060 +/− 0.020 | 0.575 +/− 0.125 |
| −0.040 +/− 0.040 | −0.270 +/− 0.052 | 0.021 +/− 0.022 | 0.050 +/− 0.060 |
| 0.035 +/− 0.040 | −0.088 +/− 0.050 | 0.102 +/− 0.023 | 0.775 +/− 0.125. |

Without wishing to be bound by any theory, it is believed that partitioning systems having these properties may be surprisingly effective for partitioning the same protein in different ways, depending on which cancer that the protein arose from. As discussed herein, in most partitioning systems, the same protein would be expected to partition in the same way, even though arising from different cancers. However, the specific partitioning systems described herein were found to be effective at partitioning the same protein in different ways.

As mentioned, in some embodiments, partitioning systems with identical or very close differences between the solvent properties of the phases may be produced using different pairs of polymers, various molecular weights and/or concentrations of polymers, nonionic additives, various types of buffers and other additives. As a non-limiting example, a partitioning system formed from 15.1 wt % Ficoll®-70 kDa, 7.9 wt % PEG-8 kDa, and 0.15 M NaCl in 0.01 M sodium phosphate buffer, pH 7.4 has a difference between the solvent dipolarity/polarizability of the coexisting phases (Δπ*) of −0.052, a difference between the solvent hydrogen bond donor acidity of the coexisting phases (Δα) value of 0.023, a difference between the solvent hydrogen bond acceptor basicity of the coexisting phases (Δβ) of −0.022, and a difference between the electrostatic properties of the coexisting phases (c) of −0.092. A partitioning system formed from 12.9 wt % Dextran-70 kDa, 17.5 wt %. Ficoll®-70 kDa, 0.10 M $Cs_2SO_4$ in 0.01 M sodium phosphate buffer, pH 7.4 has a difference between the solvent dipolarity/polarizability of the coexisting phases (Δπ*) of −0.056, a difference between the solvent hydrogen bond donor acidity of the coexisting phases (Δα) of 0.020, a difference between the solvent hydrogen bond acceptor basicity of the coexisting phases (Δβ) of −0.019, and the difference between the electrostatic properties of the coexisting phases (c) of −0.093. Thus, even though these two example partitioning systems are formed from different salts, sugars, etc., they will exhibit very similar partitioning behaviors.

As discussed, the partitioning system may, in certain embodiments, be an aqueous two-phase partitioning system or an aqueous multi-phase partitioning system, in certain embodiments. Aqueous two-phase systems may arise in aqueous mixtures of different water-soluble polymers or a single polymer and a specific salt. When two certain polymers, e.g., dextran (Dex) and polyethylene glycol (PEG), or a single certain polymer and a certain inorganic salt, e.g., polyvinylpyrrolidone (PVP) and sodium sulfate, are mixed in water above certain concentrations, the mixture separates into two immiscible aqueous phases. There is a discrete interfacial boundary separating two phases, one rich in one polymer and the other rich in the other polymer or inorganic salt. The aqueous solvent in both phases may provide media suitable for biological products. Two-phase systems can be generalized to multiple phase system by using different chemical components, and aqueous systems with a dozen or more phases have been mentioned in the literature.

Aqueous two-phase systems arise in aqueous mixtures of different water-soluble polymers or a single polymer and specific salts. For example, dextran and polyethylene glycol ("PEG") are mixed in water above certain concentrations, the mixture separates into two immiscible aqueous phases separated by a clear interfacial boundary. These two separated phases are said to have resolved. In one phase, the solution is rich in one polymer and, on the other side of this boundary in a second phase, the solution is rich in the other polymer. Other examples of aqueous two-phase systems include, but are not limited to, PEG-Ucon™ (50-HB-5100, which is a copolymer of ethylene glycol and propylene glycol), Ucon™-PVP, Ucon™-PPG (polypropylene glycol), PEG-PAM (polyacrylamide), PAM-PVP, PAM-PPG (polypropylene glycol), PEG-Ficoll® (a neutral, highly branched, high-mass, hydrophilic polymer prepared by the copolymerization of sucrose and epichlorohydrin, available from GE Healthcare), PEG-PAM (polyacrylamide), PEG-PVP, PVP-PAM, etc.

"Aqueous," as used herein, refers to the characteristic properties of a solvent/solute system wherein the solvating substance has a predominantly hydrophilic character. Examples of aqueous solvent/solute systems include those where water, or compositions containing water, is the predominant solvent.

"Aqueous multi-phase system," as used herein, refers to an aqueous system which consists of greater than one aqueous phase in which an analyte species can reside, and which can be used to characterize the structural state of the analyte species according to the methods described herein. For example, this includes aqueous system which can separate at equilibrium into two, three, or more immiscible phases. Aqueous multi-phase systems are known in the art and this phrase, as used herein, is not meant to be inconsistent with accepted meaning in the art.

Selection and modification of the types, as reflected in, for example, the chemical nature, structure, and molecular weight, of the phase-forming polymers and the concentration of the polymers can be used to vary the properties of the phases. In addition, the composition of the phases can also be changed by the addition of inorganic salts and/or organic additives. Changes to the composition of the phases can alter the properties of the phases. Examples of types of aqueous two-phase systems include, but are not limited to, dextran/PEG, dextran/polyvinylpyrrolidone, PEG/salt, and polyvinylpyrrolidone/salt.

In some embodiments, when a sample (e.g., of a biological fluid), such as serum or plasma, is added to a partitioning systems, the species present in the sample may partition between the phases independently, for example, if the species do not interact with other species or other partner that may also be present. If such an interaction takes place the species-partner complex may itself partition between the phases. The partitioning of a species (or complexes involving the species) may depend on various factors, such as the nature and 3D arrangement of the solvent-exposed groups and the properties of the coexisting phases. The 3D arrangement of the solvent-exposed groups may depend on various factors, such as the presence of salt additives, the pH, or the like. However, it should be emphasized that the exact nature of these interactions may not be known with certainty. As noted above, such portioning systems may be readily identified and/or distinguished from each other by using solvent properties such as the solvent dipolarity/polarizability difference ($\Delta\pi^*$), the solvent hydrogen bond donor acidity difference ($\Delta\alpha$), the solvent hydrogen bond acceptor basicity difference ($\Delta\beta$), and the electrostatic property difference (c) between two phases of the partitioning system, without necessarily being to identify each factor that may contribute to the interaction between a species and the phases of a partitioning system.

When a solute or other species is introduced into such a two-phase system, it distributes between the two phases. Partitioning of a solute can be quantified by the partition coefficient K defined as the ratio between the concentrations of the solute in the two immiscible phases at equilibrium. Phase separation in aqueous polymer systems may result from different effects of two polymers (or a single polymer and a salt) on the water structure. As the result of the different effects on water structure, the solvent features of aqueous media in the coexisting phases differ from one another. The difference between phases can be demonstrated, for example, by dielectric, solvatochromic, potentiometric, and partition measurements.

Without wishing to be bound by any theory, it is believed that partitioning of a species in aqueous two-phase systems depends on its three-dimensional structure and type and topography of chemical groups exposed to the solvent. Changes in the 3-D structure of a receptor induced by some effect, e.g., by binding of a ligand binding or by structural degradation, also change the topography of solvent accessible chemical groups in a species or both the topography and the type of the groups accessible to solvent. One result of these changes is an alteration in the partition behavior of the species. As a result, by monitoring the partition coefficient of a species, it is possible to detect a change in the state of a structure for which a partition coefficient is already known.

Similarly, such changes may be detected using other methods which have an underlying dependence upon the topography and/or the types of solvent accessible groups. Examples of such other methods include, but are not limited to, column liquid-liquid partition chromatography (LLCP), heterogeneous two-phase systems or a multiphase heterogeneous system.

In cases where a method as in determining a coefficient which reflects a relative partitioning, e.g., as in a partition coefficient, a single descriptor is obtained. While the many different aqueous two-phase systems all differ in their sensitivity toward various chemical groups, e.g., charged and non-polar groups, the presence of a detectable difference between two conformational states, in the form of a change in a partition coefficient, may result from a great many different mechanisms. As such, a similar change in a single partition coefficient may reflect very dissimilar conformational changes. In addition, in some cases, more than one partitioning coefficient may be obtained, e.g., as in a signature. See, e.g., U.S. Pat. No. 7,968,350, incorporated by reference in its entirety.

"Partition coefficient," as used herein, refers to the coefficient which is defined by the ratio between the concentrations of the solute in the two immiscible phases at equilibrium. For example, the partition coefficient (K) of an analyte in a two-phase system is defined as the ratio of the concentration of analyte in the first phase to that in the second phase. For multi-phase systems, there are multiple partition coefficients wherein each partition coefficient defines the ratio of analyte in first selected phase and a second selected phase. It will be recognized that the total number of partition coefficients in any multi-phase system will be equal to the total number of phases minus one.

Evaluation of data from partitioning of a species can involve use of the partition coefficient ("K"), which is defined as the ratio between the concentrations of a species in the two immiscible phases at equilibrium. For example, the partition coefficient, K, of a protein is defined as the ratio of the protein in first phase to that in the second phase in a biphasic system. When multiple phase systems are formed, there can be multiple independent partition coefficients that could be defined between any two phases. From mass balance considerations, the number of independent partition coefficients will be one less than the number of phases in the system.

It will be recognized that the partition coefficient K for a given species of a given conformation will be a constant if the conditions and the composition of the two-phase system in thermodynamic equilibrium to which it is subjected remain constant. Thus, if there are changes in the observed partition coefficient K for a protein upon addition of a potential binding partner, these changes can be presumed to result from changes in the protein structure caused by formation of a protein-binding partner complex. "K," as used herein, is used as specifically mathematically defined herein, and in all instances also includes, by definition, any coefficient representing the relative measure of interaction between a species and at least two interacting components.

The concentration of the species in each phase can be used to determine the partition coefficient, K, of the sample under the particular system conditions. Since K reflects only the ratio of the two concentrations, the absolute values are not typically required. It will be recognized that this can allow certain analytical procedures to be simplified, e.g., calibration can be eliminated in some instances.

The partition coefficient can be compared with other K values in some embodiments. For example, a K value for a species can be compared to the K values for the species under different conditions, a K value for a species can be compared to the K values for the species when combined with other species, or a set of K values for a species can be compared to other sets of K values.

In some cases, multiple partition coefficients or other metrics (e.g., for different solutes) may be assembled into a mathematical construct (e.g., a vector, a signature, a profile, a pattern, etc.) of values that can be compared against other standards (e.g., against none comparative constructs for known types of cancers), for example mathematically or statistically. The mathematical construct may comprise numbers, mathematical expressions, visual representations or other techniques. In some embodiments, a sample may also be partitioned using two or more different partitioning systems, and the partitioning behavior within the partitioning systems used to form a mathematical construct.

Thus, in certain embodiments, a pattern comprised of partition coefficients corresponding to different protein biomarkers, obtained from same or different partitioning systems, may be constructed such that it may provide specificity to the type of cancer. For example, a vector of partition coefficients for different proteins (or other species) and/or different partitioning systems may be used to determine or identify specific types of cancer. Such patterns may be determined, for example, using mathematical or statistical approaches, including machine learning, deep learning, multiple logistic regression, etc. Such patterns may be constructed in some cases, with additional parameters including clinically relevant parameters (age, race, other diagnostics information, etc.), or other species (e.g., biomarkers such as DNA, RNA, etc.).

As used herein, "signature" refers to a particular representation of desired information, which can be defined as a set of relative measures of interaction described above obtained from experiments with different interacting components. Typically, a signature is used in place of more detailed information when the latter is difficult to obtain, or when it is not necessary to completely describe such information in order to make use of it. For example, fingerprinting individual people is a well-recognized technique to uniquely identify an individual (to a reasonable certainty), providing a conveniently obtained and conveniently dense information set instead of describing the individual using other representations, e.g., genetic makeup, or by using exhaustively physical description and other information.

Different assay methods may be used, e.g., to determine a species such as a protein within one or more phase of the partitioning system. The assays will often depend upon the identity and type of the species present. Examples of suitable assay techniques include, but are not limited to, spectroscopic, immunochemical, chemical, fluorescent, radiological and enzymatic assays. When the species is a peptide or protein, common peptide or protein detection techniques can be used. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents. In other embodiments, certain immunochemical assays can be used in some cases to determine a species, for example, Enzyme Linked ImmunoSorbent Assay (ELISA).

The sample of biological fluid may be taken from a subject, and may comprise fluids such as whole blood, blood serum, blood plasma, saliva, nasal fluid, sputum, urine, CNS fluid, breast nipple aspirate fluid, cerebral spinal fluid, semen, or the like. The subject that the biological fluid is taken from may be human, or non-human, e.g., a non-human mammal. Non-human mammals include, but are not limited to, a dog, cat, horse, cow, pig, sheep, goat, chicken, primate, rat, and mouse.

As mentioned, a variety of cancers may be determined in a blood sample (or other suitable fluid sample). Examples of cancers include, but are not limited to: breast, prostate, lung, ovarian, colorectal, and brain cancer. Other non-limiting examples of cancers include biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Still other examples of cancers include lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain.

The following documents are incorporated herein by reference in their entireties: U.S. Pat. Nos. 7,968,350; 8,041,513; 8,099,242; 8,211,714; 8,437,964; 9,354,229; and 9,678,076. In addition, U.S. Provisional Patent Application Ser. No. 63/272,759, filed Oct. 28, 2021, entitled "Partitioning Systems and Methods for Determining Multiple Types of Cancers," is incorporated herein by reference in its entirety.

The following examples are intended to illustrate certain embodiments of the present disclosure, but do not exemplify the full scope of the disclosure.

Example 1

In this example, it was demonstrated that the partition coefficients of proteins in human sera from patients with different cancers differ significantly from those of the same proteins in sera from health donors, and that such differences depend on the type of cancer.

Pooled serum samples from healthy (sample identifier 0651) and ovarian cancer stage I patients (sample identifier 4850) were obtained from the Clinical Proteomics Reference Laboratory (Gaithersburg, MD). Pooled serum samples from patients with stage 1 breast cancer, patients with stage 1 pancreatic cancer, and patients with stage 1 prostate cancer were formed from individual samples obtained from Sera-Care Life Sciences and from PromedDx, Inc. Samples were obtained frozen and stored at −80° C. Diagnostic status of patients were provided by the vendors.

Multiple aqueous two-phase partitioning systems, such as the following pairs, were prepared and used to estimate the suitable coarse space per protocol: 6.1 wt % PEG-8000/12.4 wt % Dextran-70K; 16 wt % PVP-40K/15 wt % PEG-8000; 16 wt % polyacrylamide (PAM-10,000)/8 wt % PEG-8000; 15.0 wt % PVP-40K/19.0 wt % PAM-10000; and 7.9 wt % PEG-8000/15.1 wt % Ficoll®. These were all prepared with in 0.01 M sodium/potassium phosphate buffer at pH 7.4.

The aqueous two-phase system ("ATPS") was composed of two nonionic polymers, phosphate buffer, pH 7.4, and NaCl (ATPS #1). Plasma pools of breast, prostate, pancreatic and ovarian cancers, and control (normal plasma) were prepared from about 10 individual samples each. Immunoassays for protein biomarkers in Table 2 were deployed as described below. A combined sparse DOE-RSD analysis was conducted per protocol to arrive at desired solvent parameters shown in Table 1. The specific partition coefficients of the various protein biomarker candidates for the different cancers and the control samples are shown in Table 2. Details of the experimental protocol are described below. The composition corresponding to the solvent parameters in Table 2 comprised 7.9 wt % PEG-8000, 15.1 wt % Ficoll®, 0.25 M NaCl, 0.5 M arginine HCl, and 0.11 M phosphate buffer, at pH 7.4. The differences between the solvent features of the two coexisting phases were characterized and are presented below in Table 1. These were measured as described in Example 6.

The aqueous two-phase system was prepared by mixing the appropriate amounts of stock polymers, salt, and buffer solutions dispensed by liquid handling workstation Hamilton ML-4000 into a microtube of a total volume of 1.2 mL up to a total volume of a mixture of 440 microliters. 40 microliters of each serum sample were added to the system. The ratio between the volumes of the two phases of each system of a final volume of 480 microliters was as 1:1. The system was vigorously shaken and centrifuged for 45 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted 5-fold and mixed with appropriate reagents as indicated below and used for further analysis performed as described below.

The LabMAP technology (Luminex) combines the principle of a sandwich immunoassay with the fluorescent-bead based technology allowing multiplex analysis of up to 100 different analytes in a single microtiter well. The LabMAP assays were performed in 96-well microplate format according to the protocol by Biosource International (Camarillo, CA). A filter-bottom 96-well microplate (Millipore, Billerica, MA) was blocked for 10 minutes with phosphate buffer saline/bovine serum albumin solution. To generate a standard curve, 5-fold dilutions of appropriate standards were prepared in serum diluent. Standards and patient sera were pipetted at 50 microliters per well in duplicate and mixed with 50 microliters of bead mixture. The microplate was incubated for 1 hour at room temperature on a microplate shaker. Wells were then washed thrice with washing buffer using a vacuum manifold. Phicoerythrin (PE-) conjugated secondary antibody was added to the appropriate wells and the wells were incubated for 45 minutes in the dark with constant shaking. Wells were washed twice, assay buffer was added to each well, and samples were analyzed using the Bio-Plex suspension array system (Bio-Rad Laboratories, Hercules, CA). Analysis of experimental data was performed using five-parameter curve fitting. The molecular properties of the ATPS #1 are presented in Table 1 and the results expressed as the ratios of the concentration of a given antigen in the upper phase to that in the lower phase, i.e., partition coefficients, are presented in Table 2, showing the differences between the solvent features of the upper and lower phases and partition coefficients for various antigens in serum for ATPS #1.

TABLE 1

| Molecular Property | Dipolarity/ polarizability ($\Delta\pi^*$) | HBD acidity ($\Delta\alpha$) | HBA basicity ($\Delta\beta$) | Electrostatic properties (c) |
|---|---|---|---|---|
| Difference | −0.175 +/− 0.007 | 0.001 +/− 0.035 | −0.050 +/− 0.021 | 0.020 +/− 0.135 |

TABLE 2

| Biomarker | Control | Breast cancer | Ovarian cancer | Pancreatic cancer | Prostate cancer |
|---|---|---|---|---|---|
| Angiostatin | 3.45-3.55 | 3.50 | 10.2 | 10.6 | 2.68 |
| IGFBP-1 | 7.50-7.70 | 7.76 | 27.8 | 7.14 | 4.29 |
| ErbB2 | 1.10-1.20 | 1.41 | 1.0 | n/a | n/a |
| MMP2 | 18.7-19.2 | 14.7 | n/a | 10.6 | 0.29 |
| MMP9 | 11-11.5 | 12.6 | 7.92 | 9.3 | 6.53 |
| MPO | 0.20-0.30 | 0.35 | n/a | 0.19 | 0.50 |
| RANTES | 3.8-3.9 | 4.09 | 2.24 | n/a | n/a |
| SIL-6R | 8.8-9.2 | 14.1 | 6.39 | n/a | n/a |
| TSP | 1.25-1.30 | 0.89 | n/a | 2.83 | 0.32 |

IGFBP-1: Insulin Like Growth Factor Binding Protein 1; ErbB2 or Her2 is the protein member of a family of receptor tyrosine kinases structurally related to the epidermal growth factor receptor (EGFR); MMP2: matrix metallopeptidase 2; MMP9: matrix metallopeptidase 9; MPO: myeloperoxidase; RANTES: chemokine; sIL-6R: Soluble IL-6 receptor; TSP: thrombospondin.

The data presented in Table 1 show that the pattern of partition coefficients for the listed set of antigens differs between healthy controls and sera from patients with various cancers tested-breast, ovarian, pancreatic, and prostate. The pattern of an individual biomarker could be utilized to confer cancer specificity, or a set of biomarkers could be combined to derive a higher dimensional pattern with even enhanced specificity.

Example 2

In this example it was demonstrated that the partition coefficients of proteins in human sera from patients with different cancers using a different ATPS than Example 1 differ significantly from those of the same proteins in sera from health donors and that such differences depend on the type of cancer.

Pooled serum samples from healthy (sample identifier 0651) and ovarian cancer stage I patients (sample identifier 4850) were obtained from the Clinical Proteomics Reference Laboratory (Gaithersburg, MD). Pooled serum samples from patients with stage 1 breast cancer, patients with stage 1 pancreatic cancer, and patients with stage 1 prostate cancer were formed from individual samples obtained from Sera-Care Life Sciences and from PromedDx, Inc. Samples were obtained frozen and stored at −80° C. Diagnostic statuses of patients were provided by the vendors.

Multiple aqueous two-phase partitioning systems, such as the following pairs, were prepared and used to estimate the suitable coarse space per protocol: 6.1 wt % PEG-8000/12.4 wt % Dextran-70K; 12 wt % PVP-40K/17 wt % PEG-8000; 18 wt % polyacrylamide (PAM-10,000)/6 wt % PEG-8000; 15.0 wt % PVP-40K/19.0 wt % PAM-10000; and 9 wt % PEG-8000/15 wt % Ficoll®. These were all prepared with in 0.01 M sodium/potassium phosphate buffer at pH 7.4.

The aqueous two-phase system was composed of two nonionic polymers, phosphate buffer, pH 7.4, and NaCl (ATPS #2). Plasma pools of breast, prostate, pancreatic and ovarian cancers, and control (normal plasma) were prepared from about 10 individual samples each. Immunoassays for protein biomarkers in Table 4 were deployed as described below. A combined sparse DOE-RSD analysis was conducted per protocol to arrive at desired solvent parameters shown in Table 3. The specific partition coefficients of the various protein biomarker candidates for the different cancers and the control samples are shown in Table 4. Details of the experimental protocol are described below. The composition corresponding to the solvent parameters in Table 4 comprised 18.2 wt % PVP-40K, 16.5 wt % PEG-8000, 1.5 M NaCl, 1.0 M TMAO, and 0.001 M phosphate buffer, at pH 7.4. The differences between the solvent features of the two coexisting phases were characterized and are presented below in Table 3. These were measured as described in Example 6.

The aqueous two-phase system was prepared by mixing the appropriate amounts of stock polymers, salt, and buffer solutions dispensed by liquid handling workstation Hamilton ML-4000 into a microtube of a total volume of 1.2 mL up to a total volume of a mixture of 440 microliters. 40 microliters of each serum sample were added to the system. The ratio between the volumes of the two phases of each system of a final volume of 480 microliters was as 1:1. The system was vigorously shaken and centrifuged for 45 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted 5-fold and mixed with appropriate reagents as indicated below and used for further analysis performed as described below.

The LabMAP technology (Luminex) combines the principle of a sandwich immunoassay with the fluorescent-bead based technology allowing multiplex analysis of up to 100 different analytes in a single microtiter well. The LabMAP assays were performed in 96-well microplate format according to the protocol by Biosource International (Camarillo, CA). A filter-bottom 96-well microplate (Millipore, Billerica, MA) was blocked for 10 minutes with phosphate buffer saline/bovine serum albumin solution. To generate a standard curve, 5-fold dilutions of appropriate standards were prepared in serum diluent. Standards and patient sera were pipetted at 50 microliters per well in duplicate and mixed with 50 microliters of bead mixture. The microplate was incubated for 1 hour at room temperature on a microplate shaker. Wells were then washed thrice with washing buffer using a vacuum manifold. Phicoerythrin (PE-) conjugated secondary antibody was added to the appropriate wells and the wells were incubated for 45 minutes in the dark with constant shaking. Wells were washed twice, assay buffer was added to each well, and samples were analyzed using the Bio-Plex suspension array system (Bio-Rad Laboratories, Hercules, CA). Analysis of experimental data was performed using five-parameter curve fitting. The results expressed as the ratios of the concentration of a given antigen in the upper phase to that in the lower phase, i.e., partition coefficients, are presented in Table 4, which shows differences between the solvent features of the upper and lower phases and partition coefficients for various antigens in serum for ATPS #2. Table 3 describes the molecular properties of ATPS #2.

TABLE 3

| Molecular Property | Dipolarity/ polarizability ($\Delta\pi^*$) | HBD acidity ($\Delta\alpha$) | HBA basicity ($\Delta\beta$) | Electrostatic properties (c) |
|---|---|---|---|---|
| Difference | 0.005 +/− 0.008 | −0.380 +/− 0.095 | −0.020 +/− 0.019 | 0.295 +/− 0.184 |

TABLE 4

| Partition coefficients | Control | Breast cancer | Ovarian cancer | Pancreatic cancer | Prostate cancer |
|---|---|---|---|---|---|
| Angiostatin | 25.3-26.7 | 19.6 | 23.0 | 14.2 | 9.98 |
| EGFR | 6.30-7.00 | 9.17 | 7.81 | n/a | n/a |
| SICAM-1 | 14.8-15.0 | 17.8 | 8.33 | 9.10 | 8.67 |
| MMP2 | 18.2-19.2 | 21.4 | n/a | 21.2 | 17.8 |
| MMP9 | 30.1-31.2 | 33.0 | 12.1 | 19.0 | 25.0 |
| MPO | 38.4-37.2 | 23.7 | n/a | 13.0 | 7.4 |
| SVCAM-1 | 33.8-34.5 | 28.7 | 16.4 | 17.8 | 28.9 |
| SIL-6R | 8.3-9.2 | 14.3 | 11.0 | n/a | n/a |
| TSP | 9.7-10.3 | 5.96 | n/a | 4.05 | 5.32 |

EGFR: Epidermal Growth Factor Receptor; sICAM-1: Soluble intercellular adhesion molecule-1; sVCAM-1: Circulating Vascular Cell Adhesion Molecule-1; other abbreviations are given with respect to Table 1.

The data presented in Table 4 show that the pattern of partition coefficients for the listed set of antigens differs between healthy controls and sera from patients with various cancers tested-breast, ovarian, pancreatic, and prostate. These data are also different than the data presented in Table 2 for ATPS #1. The pattern of an individual biomarker could be utilized to confer cancer specificity, or a set of biomarkers could be combined to derive a higher dimensional pattern with even enhanced specificity. Furthermore, combining partitioning information from at least two different ATPS with distinct molecular properties for the same biomarker or for different biomarkers into a pattern may further enhance overall specificity.

Example 3

In this example, it was demonstrated that the partition coefficients of proteins in human sera from patients with different cancers using yet another ATPS differ significantly from those of the same proteins in sera from health donors and that such differences depend on the type of cancer.

Pooled serum samples from healthy (sample identifier 0651) and ovarian cancer stage I patients (sample identifier 4850) were obtained from the Clinical Proteomics Reference Laboratory (Gaithersburg, MD). Pooled serum samples from patients with stage 1 breast cancer, patients with stage 1 pancreatic cancer, and patients with stage 1 prostate cancer were formed from individual samples obtained from SeraCare Life Sciences and from PromedDx, Inc. Samples were obtained frozen and stored at −80° C. Diagnostic statuses of patients were provided by the vendors.

Multiple aqueous two-phase partitioning systems, such as the following pairs, were prepared and used to estimate the suitable coarse space per protocol: 14 wt % PVP-40K/16 wt % PEG-8000; 16 wt % polyacrylamide (PAM-10,000)/8 wt % PEG-8000; 14.0 wt % PVP-40K/20.0 wt % PAM-10000; and 7.9 wt % PEG-8000/15.1 wt % Ficoll®. These were all prepared with in 0.01 M sodium/potassium phosphate buffer at pH 7.4.

The aqueous two-phase system was composed of two nonionic polymers, phosphate buffer, pH 7.4, and NaSCN additive (ATPS #3). Plasma pools of breast, prostate, pancreatic and ovarian cancers, and control (normal plasma) were prepared from about 10 individual samples each. Immunoassays for protein biomarkers in Table 6 were deployed as described below. A combined sparse DOE-RSD analysis was conducted per protocol to arrive at desired solvent parameters shown in Table 5. The specific partition coefficients of the various protein biomarker candidates for the different cancers and the control samples are shown in Table 6. Details of the experimental protocol are described below. The composition corresponding to the solvent parameters in Table 6 comprised 8.7 wt % PEG-8000, 16.3 wt % Ficoll®-70, 0.75 M NaSCN, 0.5 M trehalose, and 0.11 M phosphate buffer, at pH 7.4. The differences between the solvent features of the two coexisting phases were characterized and are presented below in Table 5. These were measured as described in Example 6.

The aqueous two-phase system was prepared by mixing the appropriate amounts of stock polymers, salt, and buffer solutions dispensed by liquid handling workstation Hamilton ML-4000 into a microtube of a total volume of 1.2 mL up to a total volume of a mixture of 440 microliters. 40 microliters of each serum sample were added to the system. The ratio between the volumes of the two phases of each system of a final volume of 480 microliters was as 1:1. The system was vigorously shaken and centrifuged for 45 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted 5-fold and mixed with appropriate reagents as indicated below and used for further analysis performed as described below.

The LabMAP technology (Luminex) combines the principle of a sandwich immunoassay with the fluorescent-bead based technology allowing multiplex analysis of up to 100 different analytes in a single microtiter well. The LabMAP assays were performed in 96-well microplate format according to the protocol by Biosource International (Camarillo, CA). A filter-bottom 96-well microplate (Millipore, Billerica, MA) was blocked for 10 minutes with phosphate buffer saline/bovine serum albumin solution. To generate a standard curve, 5-fold dilutions of appropriate standards were prepared in serum diluent. Standards and patient sera were pipetted at 50 microliters per well in duplicate and mixed with 50 microliters of bead mixture. The microplate was incubated for 1 hour at room temperature on a microplate shaker. Wells were then washed thrice with washing buffer using a vacuum manifold. Phicoerythrin (PE-) conjugated secondary antibody was added to the appropriate wells and the wells were incubated for 45 minutes in the dark with constant shaking. Wells were washed twice, assay buffer was added to each well, and samples were analyzed using the Bio-Plex suspension array system (Bio-Rad Laboratories, Hercules, CA). Analysis of experimental data was performed using five-parameter curve fitting. The results expressed as the ratios of the concentration of a given antigen in the upper phase to that in the lower phase, i.e., partition coefficients, are presented in Table 6, which shows differences between the solvent features of the upper and lower phases and partition coefficients for various antigens in serum. Table 5 gives the molecular properties of ATPS #3.

TABLE 5

| Molecular Property | Dipolarity/ polarizability ($\Delta\pi^*$) | HBD acidity ($\Delta\alpha$) | HBA basicity ($\Delta\beta$) | Electrostatic properties (c) |
|---|---|---|---|---|
| Difference | −0.105 +/− 0.040 | −0.183 +/− 0.048 | 0.060 +/− 0.020 | 0.575 +/− 0.125 |

TABLE 6

| Partition coefficients | Control | Breast cancer | Ovarian cancer | Pancreatic cancer | Prostate cancer |
|---|---|---|---|---|---|
| EGFR | 11.6 | 21.5 | 12.3 | n/a | n/a |
| SICAM-1 | 12.8 | 19.5 | 11.1 | n/a | 5.1 |
| MMP2 | 17.6 | 23.3 | n/a | n/a | 9.53 |
| MPO | 3.63 | 16.1 | 11.3 | 13.5 | 1.3 |
| SVCAM-1 | 5.3 | 1.49 | 1.72 | 2.22 | 1.27 |
| EGFBP | 24.2 | 9.31 | 7.13 | 12.6 | 6.48 |
| TSP | 5.5 | 22.3 | n/a | 48 | 1.16 |

EGFBP: insulin-like growth factor binding protein; other abbreviations are given above.

The data presented in Table 6 show that the pattern of partition coefficients for the listed set of antigens differs between healthy controls and sera from patients with various cancers tested-breast, ovarian, pancreatic, and prostate. These data are also different than the data presented in Tables 2 and 4 for ATPS #1 and ATPS #2, respectively. The pattern of an individual biomarker could be utilized to confer cancer specificity, or a set of biomarkers could be combined to derive a higher dimensional pattern with even enhanced specificity. Furthermore, combining partitioning information from at least two different ATPS with distinct molecular properties for the same biomarker or for different biomarkers into a pattern may further enhance overall specificity.

Example 4

In this example, it was demonstrated that the partition coefficients of proteins in human sera from patients with different cancers in yet another ATPS differ significantly from those of the same proteins in sera from health donors and that such differences depend on the type of cancer.

Pooled serum samples from healthy (sample identifier 0651) and ovarian cancer stage I patients (sample identifier 4850) were obtained from the Clinical Proteomics Reference Laboratory (Gaithersburg, MD). Pooled serum samples from patients with stage 1 breast cancer, patients with stage 1 pancreatic cancer, and patients with stage 1 prostate cancer were formed from individual samples obtained from Sera-Care Life Sciences and from PromedDx, Inc. Samples were obtained frozen and stored at −80° C. Diagnostic statuses of patients were provided by the vendors.

Multiple aqueous two-phase partitioning systems, such as the following pairs, were prepared and used to estimate the suitable coarse space per protocol, as in Example 1: 6.1 wt % PEG-8000/12.4 wt % Dextran-70K; 16 wt % PVP-40K/15 wt % PEG-8000; 16 wt % polyacrylamide (PAM-10, 000)/8 wt % PEG-8000; 15.0 wt % PVP-40K/19.0 wt % PAM-10000; and 7.9 wt % PEG-8000/15.1 wt % Ficoll®. These were all prepared with in 0.01 M sodium/potassium phosphate buffer at pH 7.4.

The aqueous two-phase system was composed of two nonionic polymers, phosphate buffer, pH 7.4, and NaCl (ATPS #4). Plasma pools of breast, prostate, pancreatic and ovarian cancers, and control (normal plasma) were prepared from about 10 individual samples each. Immunoassays for protein biomarkers in Table 8 were deployed as described below. A combined sparse DOE-RSD analysis was conducted per protocol to arrive at desired solvent parameters shown in Table 7. The specific partition coefficients of the various protein biomarker candidates for the different cancers and the control samples are shown in Table 8. Details of the experimental protocol are described below. The composition corresponding to the solvent parameters in Table 8 comprised 17.0 wt % PVP-40K, 20.5 wt % PAM-10K, 0.25 M $Na_2SO_4$, 1.5 M TMAO, and 0.01 M phosphate buffer, at pH 7.4. The differences between the solvent features of the two coexisting phases were characterized and are presented below in Table 7. These were measured as described in Example 6.

The aqueous two-phase system was prepared by mixing the appropriate amounts of stock polymers, salt, and buffer solutions dispensed by liquid handling workstation Hamilton ML-4000 into a microtube of a total volume of 1.2 mL up to a total volume of a mixture of 440 microliters. 40 microliters of each serum sample was added to the system. The ratio between the volumes of the two phases of each system of a final volume of 480 microliters was as 1:1. The system was vigorously shaken and centrifuged for 45 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted 5-fold and mixed with appropriate reagents as indicated below and used for further analysis performed as described below.

The LabMAP technology (Luminex) combines the principle of a sandwich immunoassay with the fluorescent-bead based technology allowing multiplex analysis of up to 100 different analytes in a single microtiter well. The LabMAP assays were performed in 96-well microplate format according to the protocol by Biosource International (Camarillo, CA). A filter-bottom 96-well microplate (Millipore, Billerica, MA) was blocked for 10 minutes with phosphate buffer saline/bovine serum albumin solution. To generate a standard curve, 5-fold dilutions of appropriate standards were prepared in serum diluent. Standards and patient sera were pipetted at 50 microliters per well in duplicate and mixed with 50 microliters of bead mixture. The microplate was incubated for 1 hour at room temperature on a microplate shaker. Wells were then washed thrice with washing buffer using a vacuum manifold. Phicoerythrin (PE-) conjugated secondary antibody was added to the appropriate wells and the wells were incubated for 45 minutes in the dark with constant shaking. Wells were washed twice, assay buffer was added to each well, and samples were analyzed using the Bio-Plex suspension array system (Bio-Rad Laboratories, Hercules, CA). Analysis of experimental data was performed using five-parameter curve fitting. The results expressed as the ratios of the concentration of a given antigen in the upper phase to that in the lower phase, i.e., partition coefficients, are presented in Table 8, showing the differences between the solvent features of the upper and lower phases and partition coefficients for various antigens in serum. Table 7 illustrates the molecular properties of ATPS #4.

TABLE 7

| Molecular Property | Dipolarity/ polarizability ($\Delta\pi^*$) | HBD acidity ($\Delta\alpha$) | HBA basicity ($\Delta\beta$) | Electrostatic properties (c) |
|---|---|---|---|---|
| Difference | −0.105 +/− 0.040 | −0.183 +/− 0.048 | 0.060 +/− 0.020 | 0.575 +/− 0.125 |

TABLE 8

| Partition coefficients | Control | Breast cancer | Ovarian cancer | Pancreatic cancer | Prostate cancer |
|---|---|---|---|---|---|
| E-selectin | 0.74 | 0.38 | 0.74 | 0.64 | 1.73 |
| EGFBP-1 | 1.48 | 1.59 | 1.33 | 1.18 | 2.16 |
| SICAM-1 | 1.52 | 1.21 | 1.17 | 1.13 | 1.25 |
| MMP2 | 0.98 | 0.91 | n/a | 0.78 | 0.97 |
| MMP9 | 6.21 | 5.69 | 5.29 | 6.45 | 12.5 |
| MPO | 0.54 | 0.45 | 0.62 | 0.58 | 0.40 |
| SIL-6R | 4.42 | 2.81 | 2.76 | n/a | n/a |
| TSP | 11.5 | 10.5 | 28.7 | 11.8 | 0.05 |

All abbreviations are given in above Tables.

The data presented in Table 8 show that the pattern of partition coefficients for the listed set of antigens differs between healthy controls and sera from patients with various cancers tested-breast, ovarian, pancreatic, and prostate. These data are also different than the data presented in Tables 2, 4, and 6 for ATPS #1, ATPS #2, and ATPS #3, respectively. The pattern of an individual biomarker could be utilized to confer cancer specificity, or a set of biomarkers could be combined to derive a higher dimensional pattern with even enhanced specificity. Furthermore, combining partitioning information from at least two different ATPS with distinct molecular properties for the same biomarker or for different biomarkers into a pattern may further enhance overall specificity.

Example 5

In this example, it was demonstrated that the partition coefficients of proteins in human sera from patients with different cancers differ in yet another ATPS significantly from those of the same proteins in sera from health donors and that such differences depend on the type of cancer.

Pooled serum samples from healthy (sample identifier 0651) and ovarian cancer stage I patients (sample identifier 4850) were obtained from the Clinical Proteomics Reference Laboratory (Gaithersburg, MD). Pooled serum samples from patients with stage 1 breast cancer, patients with stage 1 pancreatic cancer, and patients with stage 1 prostate cancer were formed from individual samples obtained from Sera-Care Life Sciences and from PromedDx, Inc. Samples were obtained frozen and stored at −80° C. Diagnostic statuses of patients were provided by the vendors.

Multiple aqueous two-phase partitioning systems, such as the following pairs, were prepared and used to estimate the suitable coarse space per protocol, as in Example 3: 14 wt % PVP-40K/16 wt % PEG-8000; 16 wt % polyacrylamide (PAM-10,000)/8 wt % PEG-8000; 14.0 wt % PVP-40K/20.0 wt % PAM-10000; and 7.9 wt % PEG-8000/15.1 wt % Ficoll®. These were all prepared with in 0.01 M sodium/potassium phosphate buffer at pH 7.4.

The aqueous two-phase system was composed of two nonionic polymers, phosphate buffer, pH 7.4 (ATPS #5). Plasma pools of breast, prostate, pancreatic and ovarian cancers, and control (normal plasma) were prepared from about 10 individual samples each. Immunoassays for protein biomarkers in Table 10 were deployed as described below. A combined sparse DOE-RSD analysis was conducted per protocol to arrive at desired solvent parameters shown in Table 9. The specific partition coefficients of the various protein biomarker candidates for the different cancers and the control samples are shown in Table 10. Details of the experimental protocol are described below. The composition corresponding to the solvent parameters in Table 10 comprised 8.0 wt % PEG-8000, 15.5 wt % Ficoll®-70, and 18.0 wt % phosphate buffer, at pH 7.4. The differences between the solvent features of the two coexisting phases were characterized and are presented below in Table 9. These were measured as described in Example 6.

The aqueous two-phase system was prepared by mixing the appropriate amounts of stock polymers, salt, and buffer solutions dispensed by liquid handling workstation Hamilton ML-4000 into a microtube of a total volume of 1.2 mL up to a total volume of a mixture of 440 microliters. 40 microliters of each serum sample were added to the system. The ratio between the volumes of the two phases of each system of a final volume of 480 microliters was as 1:1. The system was vigorously shaken and centrifuged for 45 min at 3500 g in a refrigerated centrifuge with a microplate rotor with the temperature maintained at 23° C. to speed the phase settling. Microtubes were taken out of the centrifuge, and aliquots of 40 microliters from the top and the bottom phases were withdrawn in duplicates and each diluted 5-fold and mixed with appropriate reagents as indicated below and used for further analysis performed as described below.

The LabMAP technology (Luminex) combines the principle of a sandwich immunoassay with the fluorescent-bead based technology allowing multiplex analysis of up to 100 different analytes in a single microtiter well. The LabMAP assays were performed in 96-well microplate format according to the protocol by Biosource International (Camarillo, CA). A filter-bottom 96-well microplate (Millipore, Billerica, MA) was blocked for 10 minutes with phosphate buffer saline/bovine serum albumin solution. To generate a standard curve, 5-fold dilutions of appropriate standards were prepared in serum diluent. Standards and patient sera were pipetted at 50 microliters per well in duplicate and mixed with 50 microliters of bead mixture. The microplate was incubated for 1 hour at room temperature on a microplate shaker. Wells were then washed thrice with washing buffer using a vacuum manifold. Phicoerythrin (PE-) conjugated secondary antibody was added to the appropriate wells and the wells were incubated for 45 minutes in the dark with constant shaking. Wells were washed twice, assay buffer was added to each well, and samples were analyzed using the Bio-Plex suspension array system (Bio-Rad Laboratories, Hercules, CA). Analysis of experimental data was performed using five-parameter curve fitting. The results expressed as the ratios of the concentration of a given antigen in the upper phase to that in the lower phase, i.e., partition coefficients, are presented in Table 10, showing the differences between the solvent features of the upper and lower phases and partition coefficients for various antigens in serum. Table 9 shows the molecular properties of ATPS #5.

TABLE 9

| Molecular Property | Dipolarity/ polarizability ($\Delta\pi^*$) | HBD acidity ($\Delta\alpha$) | HBA basicity ($\Delta\beta$) | Electrostatic properties (c) |
|---|---|---|---|---|
| Difference | 0.035 +/− 0.040 | −0.088 +/− 0.050 | 0.102 +/− 0.023 | 0.775 +/− 0.125 |

TABLE 10

| Partition coefficients | Control | Breast cancer | Ovarian cancer | Pancreatic cancer | Prostate cancer |
|---|---|---|---|---|---|
| EGFR | 0.81 | 1.31 | 1.59 | n/a | n/a |
| RANTES | 14.2 | 8.79 | 13.9 | n/a | n/a |

TABLE 10-continued

| Partition coefficients | Control | Breast cancer | Ovarian cancer | Pancreatic cancer | Prostate cancer |
|---|---|---|---|---|---|
| MMP2 | 3.23 | 0.87 | n/a | 4.92 | 5.92 |
| MMP9 | 2.81 | 3.62 | n/a | 10.1 | n/a |

RANTES: selective attractant for memory T lymphocytes and monocytes; other abbreviations are given in above Tables.

The data presented in Table 8 show that the pattern of partition coefficients for the listed set of antigens differs between healthy controls and sera from patients with various cancers tested-breast, ovarian, pancreatic, and prostate. These data are also different than the data presented in Table 2, 4, 6, and 8 for ATPS #1, ATPS #2, ATPS #3, and ATPS #4, respectively. The pattern of an individual biomarker could be utilized to confer cancer specificity, or a set of biomarkers could be combined to derive a higher dimensional pattern with even enhanced specificity. Furthermore, combining partitioning information from at least two different ATPS with distinct molecular properties for the same biomarker or for different biomarkers into a pattern may further enhance overall specificity.

Example 6

This example illustrates the determination of certain molecular solvent properties used in Examples 1-5.

The solvatochromic probes 4-nitroanisole, 4-nitrophenol, and Reichardt's carboxylated betaine dye were used to measure the dipolarity/polarizability ($\pi^*$), hydrogen bond acceptor (HBA) basicity ($\beta$), and hydrogen bond donor (HBD) acidity ($\alpha$), of a media in the separated phases of an aqueous two-phase system ("ATPS").

One non-limiting example procedure for determining these parameters is as follows.

1. Aqueous solutions (ca. 10 mM) of each solvatochromic dye were prepared and 10-20 microliters of each was added separately to a total volume of 500 microliters of a given phase of ATPS.

2. A strong base was added to the samples (~5 microliters of 1 M NaOH to 500 microliters of a given phase) containing Reichardt's carboxylated betaine dye to ensure a basic pH.

3. A strong acid (~10 microliters of 1 M HCl to 500 microliters of the phase) was added to the samples containing 4-nitrophenol in order to eliminate charge-transfer bands of the phenolate anion that were observed in some solutions.

4. The respective blank phases without dye were prepared separately.

5. The samples were homogenized in a vortex mixer and the absorption spectrum of each solution measured. To confirm reproducibility, and avoid possible aggregation or other specific interaction effects, the position of the band maximum in each sample was measured in five separate aliquots. A UV-VIS microplate reader spectrophotometer SpectraMax Plus384 (Molecular Devices, Sunnyvale, CA, USA) with a bandwidth of 2.0 nm, data interval of 1 nm, and −0.5 nm/s high resolution scan acquired the UV-Vis molecular absorbance data. Measured absorption spectra covered the range from 240 to 600 nm. A baseline reference was established by scanning the black phase of ATPS without dye. The wavelength of maximum absorbance in each phase was determined using PeakFit software package (Systat Software Inc., San Jose, CA, USA), and averaged. Standard deviations for the measured maximum absorption wavelength were less than 0.4 nm for all dyes in all solutions examined.

The maximum observed shifts in three solvents, water, n-hexane, and methanol for different concentrations of 4-nitrophenol with and without HCl, and for Reichardt's carboxylated betaine dye with and without NaOH, corresponded within experimental errors to literature values.

To determine the solvent dipolarity/polarizability $\pi^*$, the value of $\pi^*$ was determined from the wave number ($v_1$) of the longest wavelength absorption band of the 4-nitroanisole dye using the relationship:

$$\pi^* = 0.427(34.12 - v_1).$$

To determine the solvent hydrogen-bond acceptor basicity ($\beta$, values were determined from the wave number ($v_2$) of the longest wavelength absorption band of the 4-nitrophenol dye using the relationship:

$$\beta = 0.346(35.045 - v_2) - 0.577^*.$$

To determine the solvent hydrogen-bond donor acidity $\alpha$, $\alpha$ values were determined from the longest wavelength absorption band of Reichardt's betaine dye using the relationship:

$$\alpha = as\ 0.0649\ E_T(30) - 2.03 - 0.727^*.$$

The $E_T(30)$ are based on the solvatochromic pyridinium N-phenolate betaine dye (Reichardt's dye) as the probe, and are obtained directly from the wavelength ($\lambda$, nm) of the absorption band of the carboxylated form, as:

$$E_T(30) = (1/0.932)[(28591/\lambda) - 3.335].$$

The difference between the electrostatic properties of the coexisting phases (c) may be determined in each ATPS by partitioning a homologous series of sodium salts of dinitrophenylated (DNP) amino acids with the aliphatic alkyl side-chains of the increasing length, alanine, norvaline, norleucine, and alpha-amino-n-octanoic acid. The logarithms of the partition coefficients of these compounds were regressed against the length of the side-chain expressed in equivalent number of methylene groups, $N_c$. The $N_c$ values for the DNP-amino acids used are: DNP-ALA Na=1.31, DNP-norvaline Na=2.65, DNP-norleucine Na=3.75, and DNP-alpha-amino-n-octanoic acid Na=6.30. The regression equation is:

$$\log_{10} K_{DNP-AA} = c + E^* N_c,$$

where $K_{DNP-AA}$ is the partition coefficient of a DNP-amino acids Na-salt; $N_c$ is the equivalent number of $CH_2$ groups in the side-chain, and $E_i$ and $c_i$ are constants for a given ATPS system. This parameter may be used to determine the difference between the relative hydrophobicity and electrostatic properties of the phases.

Example 7

This example demonstrates one protocol for determining parameters such as $\Delta\pi^*$, $\Delta\alpha$, $\Delta\beta$, and c, representing the differences between the solvent properties of two phases of a partition system. These parameters generally measure solvent dipolarity/polarizability, hydrogen-bond donor acidity, hydrogen-bond acceptor basicity, and electrostatic properties, respectively. This example protocol generally relies on the following steps:

Initially, coarse determination of chemical components for constructing candidates suitable for aqueous two-phase partitioning systems. This allows basic chemical ingredients to be selected that would produce an aqueous two-phase partitioning system, with a range of partition coefficients of the target protein biomarkers of 0.1-10.

Such partition coefficients may allow for practical compatibility with a final analytical assay. A very small or a very large initial partition coefficient could result in a significant proportion of clinical samples being outside the range of useful analytical detection, especially for low abundance protein biomarkers of interest that may be associated with early cancer detection. For instance, these may be at very low concentration sin circulating fluids such as blood.

In general, aqueous two-phase partitioning systems that are formed by two non-ionic polymers resulting in small differences between the overall solvent properties of the two phases are desired. Systems for efficient optimization of chemical components in this step include the use of ingredients that differ regarding their hydrophobic character, e.g., PEG-Ucon™, Ucon™-PVP, Ucon™-PPG, PEG-PAG, PAG-PVP, PAG-PPG, etc. for hydrophobic proteins, and/or the use of ingredients such as PEG-Ficoll®, PEG-PAM, PEG-PVP, PVP-PAM, etc. for hydrophilic proteins.

Since aqueous two-phase systems that are composed from different starting chemical ingredients may correspond to the same difference in their solvent properties, it is not critical at this step to optimize the partitioning behavior of the proteins of interest. It may be sufficient to ascertain that their range of partitioning behaviors lie within an acceptable analytical range.

Next is to provide a coarse mapping of the set of differences between the two desired clinical states, e.g., cancer and benign phenotypes, in the general 4D parameter space in order to determine a partitioning landscape of the target protein using solvent parameters $\Delta\pi^*$, $\Delta\alpha$, $\Delta\beta$, and c. This is not prohibitive. The samples used are commonly prepared by pooling about 20 or more individual samples corresponding to a particular disease phenotype. This provides for averaged representation of the inherently heterogeneous nature of the disease on the molecular level amongst individuals. Other information available about the individual target proteins assists in the initial selection of the parameter space, e.g., the protein isoelectric points may be used to narrow pH, etc. In general, Design of Experiments (DOE) techniques can be used to map the parameter space. Examples of chemical additives that could be used to vary solvent parameters include salts (affecting the differences between electrostatic properties of the phases) and osmolytes, such as trimethylamine N-oxide (TMAO), glucose, trehalose, arginine, lysine, etc. Some additives, e.g., TMAO, may affect the difference between solvent-solvent hydrogen-bond donor acidity ($\Delta\alpha$) and solvent hydrogen-bond acceptor basicity ($\Delta\beta$) and affect only slightly dipole-dipole interactions, dipolarity/polarizability ($\Delta\pi^*$) of water between the coexisting phases. Other additives can also be used to modify the solvent parameters.

Once the partitioning landscape in the solvent parameter space has been mapped, one or more optimization techniques may be used to determine an optimal point in the parameter space to achieve an overall degree of separation between the clinical phenotypes. Such techniques are known to those of ordinary skill in the art, including Response Surface methodologies, and various simple linear as well as nonlinear interpolation techniques, etc. In some cases, more than one function may be simultaneously optimized. For example, maintaining the partition coefficients for both clinical phenotypes near unity while maximizing the difference between their values may be one such dual objective function design to simultaneously achieve both analytical and clinical objectives. Also, an objective function optimizing across multiple biomarkers instead of a single biomarker is computationally straightforward. For example, iterative directional optimization following initial sampling of the solvent parameter space can be used. This process does not require extensive or blind experimentation or trial-and-error approaches.

Next, the performance of the aqueous two-phase partitioning system specified in terms of its solvent properties may be tested with two groups of samples representing the clinical phenotypes of interest. This step typically includes statistically significant number of samples from each type, e.g., 50-100, and the results are analyzed using conventional statistical techniques such as Receiver-Operating Characteristics (ROC) analysis to examine the trade-off between sensitivity and specificity. Further optimization could also be performed at this step.

This example allows one to arrive at a set of solvent properties that underlie the partitioning behavior of a target protein. Differences between the partitioning behavior of the same protein corresponding to two different clinical phenotypes can be identified, e.g., different isoforms, etc. In this example, a general understanding can be achieved as to the role of various chemical constituents on the formation and modification of aqueous two-phase partitioning systems without requiring an exhaustive search of every possible polymer type, molecular weight, salt, additive, etc. Once an optimal composition has been identified, e.g., using the above protocol, one or more candidate sets of chemical ingredients for forming a system with those solvent properties can be readily identified. This also may allow for measuring solvent properties, allowing for pre-calibration of a set of aqueous two-phase partitioning systems with respect to their solvent properties to construct a "combinatorial library" for later use.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of"

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:

an aqueous two-phase partitioning system having a first phase and a second phase, wherein the aqueous two-phase partitioning system has:

(i) a solvent dipolarity/polarizability difference between the first phase and the second phase ($\Delta\pi^*$) of $-0.175+/-0.007$, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$;

(ii) a solvent hydrogen bond donor acidity difference between the first phase and the second phase ($\Delta\alpha$) of $0.001+/-0.035$, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932)\,[(28591/\lambda)-3.335]$, and calculating $\alpha$ in each phase as $0.0649\,E_T(30)-2.03-0.72\pi^*$;

(iii) a solvent hydrogen bond acceptor basicity difference between the first phase and the second phase ($\Delta\beta$) of $-0.050+/-0.021$, wherein $\Delta\beta$ is determined as a difference between hydrogen bond acceptor basicity ($\beta$) of the first phase and the second phase, and $\beta$ is determined separately in each phase by measuring a wavenumber ($v_2$) in cm$^{-1}$ of a longest wavelength absorption band of 4-nitrophenol in each phase, and calculating $\beta$ in each phase as $0.346(35.045-v_2)-0.577\pi^*$; and (iv) an electrostatic property difference between the first phase and the second phase (c) of $0.020+/-0.135$, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E\,N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated a-amino-n-octanoic acid, Na salt | 6.30. |

2. A composition, comprising:
an aqueous two-phase partitioning system having a first phase and a second phase, wherein the aqueous two-phase partitioning system has:
(i) a solvent dipolarity/polarizability difference between the first phase and the second phase ($\Delta\pi^*$) of 0.005+/−0.008, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$;
(ii) a solvent hydrogen bond donor acidity difference between the first phase and the second phase ($\Delta\alpha$) of −0.380+/−0.095, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932)[(28591/\lambda)-3.335]$, and calculating $\alpha$ in each phase as $0.0649\ E_T(30)-2.03-0.72\pi^*$;
(iii) a solvent hydrogen bond acceptor basicity difference between the first phase and the second phase ($\Delta\beta$) of −0.020+/−0.019, wherein $\Delta\beta$ is determined as a difference between hydrogen bond acceptor basicity ($\beta$) of the first phase and the second phase, and $\beta$ is determined separately in each phase by measuring a wavenumber ($v_2$) in cm$^{-1}$ of a longest wavelength absorption band of 4-nitrophenol in each phase, and calculating $\beta$ in each phase as $0.346(35.045-v_2)-0.577\pi^*$; and
(iv) an electrostatic property difference between the first phase and the second phase (c) of 0.295+/−0.184, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E\ N_c$ to determine c and E,
wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated a-amino-n-octanoic acid, Na salt | 6.30. |

3. A composition, comprising:
an aqueous two-phase partitioning system having a first phase and a second phase, wherein the aqueous two-phase partitioning system has:
(i) a solvent dipolarity/polarizability difference between the first phase and the second phase ($\Delta\pi^*$) of −0.105+/−0.040, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$;
(ii) a solvent hydrogen bond donor acidity difference between the first phase and the second phase ($\Delta\alpha$) of −0.183+/−0.048, wherein $\Delta\alpha$ is determined as a difference between hydrogen bond donor acidity ($\alpha$) of the first phase and the second phase, and a is determined separately in each phase by measuring a maximum wavelength ($\lambda$) in nm of an absorption band of carboxylated pyridinium N-phenolate betaine in each phase, calculating a solvent polarity ($E_T(30)$) in each phase as $(1/0.932)[(28591/\lambda)-3.335]$, and calculating $\alpha$ in each phase as $0.0649\ E_T(30)-2.03-0.72\pi^*$;
(iii) a solvent hydrogen bond acceptor basicity difference between the first phase and the second phase ($\Delta\beta$) of 0.060+/−0.020, wherein $\Delta\beta$ is determined as a difference between hydrogen bond acceptor basicity ($\beta$) of the first phase and the second phase, and $\beta$ is determined separately in each phase by measuring a wavenumber ($v_2$) in cm$^{-1}$ of a longest wavelength absorption band of 4-nitrophenol in each phase, and calculating $\beta$ in each phase as $0.346(35.045-v_2)-0.577\pi^*$; and
(iv) an electrostatic property difference between the first phase and the second phase (c) of 0.575+/−0.125, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K = c + E\ N_c$ to determine c and E,
wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated a-amino-n-octanoic acid, Na salt | 6.30. |

4. A composition, comprising:
an aqueous two-phase partitioning system having a first phase and a second phase, wherein the aqueous two-phase partitioning system has:
(i) a solvent dipolarity/polarizability difference between the first phase and the second phase ($\Delta\pi^*$) of −0.040+/−0.040, wherein $\Delta\pi^*$ is determined as a difference between dipolarity/polarizability ($\pi^*$) of the first phase and the second phase, and $\pi^*$ is determined separately in each phase by measuring a wavenumber ($v_1$) in cm$^{-1}$ of a longest wavelength absorption band of 4-nitroanisole in each phase, and calculating $\pi^*$ in each phase as $0.427(34.12-v_1)$;
(ii) a solvent hydrogen bond donor acidity difference between the first phase and the second phase ($\Delta\alpha$) of −0.270+/−0.052, wherein $\Delta\alpha$ is determined as a difference between hydrogen bond donor acidity ($\alpha$) of the first phase and the second phase, and a is determined separately in each phase by measuring a maximum wavelength (λ) in nm of an absorption band of carboxylated pyridinium N-phenolate betaine in each phase, calculating a solvent polarity ($E_T(30)$) in each phase as $(1/0.932) [(28591/\lambda)-3.335]$, and calculating α in each phase as $0.0649 E_T(30)-2.03-0.72\pi*$;

(iii) a solvent hydrogen bond acceptor basicity difference between the first phase and the second phase (Δβ) of 0.021+/-0.022, wherein Δβ is determined as a difference between hydrogen bond acceptor basicity (β) of the first phase and the second phase, and β is determined separately in each phase by measuring a wavenumber ($v_2$) in $cm^{-1}$ of a longest wavelength absorption band of 4-nitrophenol in each phase, and calculating β in each phase as $0.346(35.045-v_2)-0.577\pi*$; and (iv) an electrostatic property difference between the first phase and the second phase (c) of 0.050+/-0.060, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K=c+E\ N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated a-amino-n-octanoic acid, Na salt | 6.30. |

5. A composition, comprising:

an aqueous two-phase partitioning system having a first phase and a second phase, wherein the aqueous two-phase partitioning system has:

(i) a solvent dipolarity/polarizability difference between the first phase and the second phase (Δπ*) of 0.035+/-0.040, wherein Δπ* is determined as a difference between dipolarity/polarizability (π*) of the first phase and the second phase, and π* is determined separately in each phase by measuring a wavenumber ($v_1$) in $cm^{-1}$ of a longest wavelength absorption band of 4-nitroanisole in each phase, and calculating π* in each phase as $0.427(34.12-v_1)$;

(ii) a solvent hydrogen bond donor acidity difference between the first phase and the second phase (Δα) of -0.088+/-0.050, wherein Δα is determined as a difference between hydrogen bond donor acidity (α) of the first phase and the second phase, and a is determined separately in each phase by measuring a maximum wavelength (λ) in nm of an absorption band of carboxylated pyridinium N-phenolate betaine in each phase, calculating a solvent polarity ($E_T(30)$) in each phase as $(1/0.932) [(28591/\lambda)-3.335]$, and calculating α in each phase as $0.0649 E_T(30)-2.03-0.72\pi*$;

(iii) a solvent hydrogen bond acceptor basicity difference between the first phase and the second phase (Δβ) of 0.102+/-0.023, wherein Δβ is determined as a difference between hydrogen bond acceptor basicity (β) of the first phase and the second phase, and β is determined separately in each phase by measuring a wavenumber ($v_2$) in $cm^{-1}$ of a longest wavelength absorption band of 4-nitrophenol in each phase, and calculating β in each phase as $0.346(35.045-v_2)-0.577\pi*$; and (iv) an electrostatic property difference between the first phase and the second phase (c) of 0.775+/-0.125, wherein c is determined by separately partitioning each dinitrophenylated amino acid sodium salt in Table I in the aqueous two-phase partitioning system, measuring the partitioning coefficient (K) of each sodium salt, and regressing K and methylene group equivalents ($N_c$) of each sodium salt from Table I to $\log_{10} K=c+E\ N_c$ to determine c and E, wherein Table I is:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated a-amino-n-octanoic acid, Na salt | 6.30. |

\* \* \* \* \*

UNITED STATES PATENT AND TRADEMARK OFFICE
CERTIFICATE OF CORRECTION

| | |
|---|---|
| PATENT NO. | : 11,796,544 B1 |
| APPLICATION NO. | : 18/030849 |
| DATED | : October 24, 2023 |
| INVENTOR(S) | : Arnon Chait et al. |

It is certified that error appears in the above-identified patent and that said Letters Patent is hereby corrected as shown below:

In the Claims

At Column 32, Line 41, Claim 1 should read:
-- first phase and the second phase, and $\alpha$ is determined --

At Column 33, Lines 2-10, Table I of Claim 1 should read:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated $\alpha$-amino-$n$-octanoic acid, Na salt | 6.30. |

--

At Column 33, Line 28, Claim 2 should read:
-- first phase and the second phase, and $\alpha$ is determined --

Signed and Sealed this
Sixteenth Day of April, 2024

Katherine Kelly Vidal
*Director of the United States Patent and Trademark Office*

At Column 33, Lines 55-63, Table I of Claim 2 should read:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-$n$-octanoic acid, Na salt | 6.30. |

At Column 34, Line 14, Claim 3 should read:
-- first phase and the second phase, and α is determined --

At Column 34, Lines 41-49, Table I of Claim 3 should read:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-$n$-octanoic acid, Na salt | 6.30. |

At Column 34, Line 67, Claim 4 should read:
-- first phase and the second phase, and α is determined --

At Column 35, Lines 27-35, Table I of Claim 4 should read:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-$n$-octanoic acid, Na salt | 6.30. |

At Column 36, Line 8, Claim 5 should read:
-- first phase and the second phase, and α is determined --

At Column 36, Lines 36-44, Table I of Claim 5 should read:

TABLE I

| Salt | $N_c$ |
|---|---|
| dinitrophenylated alanine, Na salt | 1.31 |
| dinitrophenylated norvaline, Na salt | 2.65 |
| dinitrophenylated norleucine, Na salt | 3.75 |
| dinitrophenylated α-amino-*n*-octanoic acid, Na salt | 6.30. |